United States Patent
Ma et al.

(10) Patent No.: US 10,947,189 B2
(45) Date of Patent: Mar. 16, 2021

(54) ONLINE CONTINUOUS FLOW PROCESS FOR THE SYNTHESIS OF ORGANIC PEROXIDES USING HYDROGEN PEROXIDE AS RAW MATERIAL

(71) Applicant: Shanghai Hybrid-chem Technologies, Shanghai (CN)

(72) Inventors: Bing Ma, Shanghai (CN); Shuai Pan, Shanghai (CN); Xinlin Shu, Shanghai (CN)

(73) Assignee: SHANGHAI HYBRID-CHEM TECHNOLOGIES, Shanghai (CN)

( * ) Notice: Subject to any disclaimer, the term of this patent is extended or adjusted under 35 U.S.C. 154(b) by 0 days.

(21) Appl. No.: 16/787,022

(22) Filed: Feb. 11, 2020

(65) Prior Publication Data
US 2020/0172478 A1    Jun. 4, 2020

Related U.S. Application Data

(63) Continuation of application No. PCT/CN2018/100109, filed on Aug. 10, 2018.

(30) Foreign Application Priority Data

Aug. 12, 2017  (CN) .......................... 201710688666.4
Aug. 6, 2018   (CN) .......................... 201810887768.3

(51) Int. Cl.
*C07C 407/00*   (2006.01)
*B01J 19/00*    (2006.01)
*C07C 409/04*   (2006.01)
*C07C 409/36*   (2006.01)

(52) U.S. Cl.
CPC ......... *C07C 407/00* (2013.01); *B01J 19/0006* (2013.01); *B01J 2219/00051* (2013.01); *B01J 2219/00166* (2013.01); *C07C 409/04* (2013.01); *C07C 409/36* (2013.01)

(58) Field of Classification Search
CPC .... C07C 407/00; C07C 409/04; C07C 409/36
See application file for complete search history.

(56) References Cited

U.S. PATENT DOCUMENTS

| | | | | |
|---|---|---|---|---|
| 3,950,375 A * | 4/1976 | McKee | ................. | C07C 407/00 558/264 |
| 4,075,236 A | 2/1978 | Wagle et al. | | |
| 7,968,753 B2 * | 6/2011 | Azzawi | ................. | C07C 407/00 568/566 |

FOREIGN PATENT DOCUMENTS

| | | |
|---|---|---|
| CN | 101287704 A | 10/2008 |
| CN | 101023058 B | 5/2011 |
| CN | 101479239 B | 5/2013 |
| CN | 104370789 A | 2/2015 |
| CN | 107698479 A | 2/2018 |
| CN | 108250176 A | 7/2018 |
| CN | 101298429 B | 10/2019 |

OTHER PUBLICATIONS

ISR corresponding to PCT/CN2018/100109, dated Nov. 9, 2019.

* cited by examiner

*Primary Examiner* — Sikarl A Witherspoon

(57) ABSTRACT

An online continuous flow production process for directly preparing organic peroxides by using hydrogen peroxide as a raw material. This production process uses hydrogen peroxide, catalyst, and an oxidation substrate as a raw material. Substrate will be turned to designated peroxides sequentially through oxidation and workup. This process is performed in a plug-and-produce integrated continuous flow reactor, and the raw materials are continuously fed to the reactor. So, specified peroxide can be continuously obtained at the outlet of the plug-and-produce integrated continuous flow reactor.

18 Claims, 1 Drawing Sheet

ONLINE CONTINUOUS FLOW PROCESS FOR THE SYNTHESIS OF ORGANIC PEROXIDES USING HYDROGEN PEROXIDE AS RAW MATERIAL

CROSS REFERENCE TO RELATED APPLICATIONS

This application is a continuation of PCT Patent Application No. PCT/CN2018/100109, filed on Aug. 10, 2018, entitled "Online Continuous Flow Process for the Synthesis of Organic Peroxides Using Hydrogen Peroxide as Raw Material," which claims foreign priority of China Patent Application No. 201710688666.4, filed Aug. 12, 2017 and No. 201810887768.3, filed Aug. 6, 2018, in the China National Intellectual Property Administration, the entire contents of which are hereby incorporated by reference in their entireties.

FIELD OF THE DISCLOSURE

The disclosure relates to the field of chemical engineering, particularly an online continuous flow synthesis process of organic peroxides using hydrogen peroxide as raw material.

BACKGROUND OF THE DISCLOSURE

Organic peroxides are derivatives in which one or two hydrogen atoms in hydrogen peroxide are replaced by an organic group, which is generally defined as R—O—O—R. Since the first synthesis of benzoyl peroxide by Brudie in 1858, it has experienced more than 100 years. Up to today, there are more than 70 varieties of organic peroxides have been industrialized abroad.

Due to the special structure of organic peroxides, peroxy bonds are easy to split and generate free radicals under the conditions of light or heating, which determines that the peroxides have the following application:

1. The Initiator of Free Radical Polymerization

The most important application of organic peroxides is as the initiator of free radical polymerization. At present, the initiators for all the productions of PVC, PS, LDPE, PVA, coating resins, super absorbent resins, and some adhesives (such as special anaerobic adhesives) are organic peroxides.

2. The Curing Initiator for Unsaturated Polyester

Unsaturated polyester resins are generally linear polymers formed by the polycondensation of unsaturated dibasic acids, saturated dibasic acids, and glycols. Organic peroxides are the general curing initiator for this type of reaction.

3. The Crosslinker pf Polymer

In addition to the above applications, organic peroxides can also be used as the crosslinking agents for the productions of LDPE, ethylene-vinyl acetate copolymer (EVA), ethylene-propylene rubber (EPDM), and other synthetic rubbers.

4. The Degradation Agent to Prepare Special Polymers

This is a new use of organic peroxides. For example, the organic peroxides are used to chemically modify the basic PP resin to produce a high-flow PP resin with a narrow molecular weight distribution and a large melt flow index, which is also known as controlled rheology PP (CRPP). The mechanism is as follows: the organic peroxide is induced to decompose and generate free radicals; the free radicals take away the hydrogen atoms on the tertiary carbon atoms of the PP molecular chains to produce PP molecular chains with free radicals; then β-fracture occurs to obtain molecules with lower molecular weight chain; and then the degradation reaction continues with the chain transfer, and finally the free radicals undergo compounding and joining reactions to stop the degradation reaction. At present, many resin companies in the world have adopted this method and put it into industrial production. In addition, one of the main ways to prepare PP wax is the degradation of basic PP resin by using organic peroxides as the degradation agent.

5. The Oxidant for Organic Synthesis Reaction

At present, the so-called Hakan method mainly refers to the preparation of propylene oxide by using propylene as raw material and t-butyl hydroperoxide (TBHP) or phenethyl hydrogen peroxide as oxidant. Recently, more and more synthetic reactions use the organic peroxides as oxidant, such as the oxidations of cyclohexane to cyclohexanol, cyclohexanone and adipic acid, in which the catalyst is zeolite and the oxdiant is any one of tert-butyl or cyclohexyl or cumyl hydrogen peroxides. Similarly, the oxidations of saturated and unsaturated alcohols to the corresponding carbonyl compounds under microwave irradiation, use the molecular sieves as the catalysts and t-butyl hydroperoxide as the oxidant.

6. Fungicide, Bleach and Other Applications

Since the decomposition of peroxides can liberate active oxygen, organic peroxides are good enough to be used as fungicides and bleaches. For example, peracetic acid has a high-efficiency and rapid killing effect on bacterial propagules, spore fungi, and yeasts. Thus, it can be used as a fungicide for the prevention and control of infectious diseases, drinking water disinfection, and food disinfection. Organic peroxides are also formulated as 0.2% to 0.4% aqueous solution, which is widely used in disinfection of medical devices and the food industry. In addition, peracetic acid is often used as a bleaching agent for textiles, paper, grease, paraffin and starch; benzoyl peroxide is also commonly used in industry as a bleaching agent, decolorant, bactericide, and cleaning agent; succinic acid and methyl ethyl ketone peroxide are not only important germicides, but also the additives of heavy diesel fuel.

To sum up, the applications of organic peroxides are extremely wide, so developing a continuous process for the synthesis of organic peroxides has practical significance and great prospects.

The organic peroxide synthesis reaction process has several significant characteristics: Firstly, this type of reaction is strongly exothermic, whether the reaction using hydrogen peroxide and alcohol, alkane, carboxylic acid or anhydride to synthesize alkyl peroxide, dialkyl peroxide or peroxycarboxylic acid; or the reaction using hydrogen peroxide and acid chloride, chloroformate or ketone to synthesize diacyl peroxide, peroxydicarbonate or peroxydiketal. Thus, the reaction device needs to have a good heat exchange to ensure that the temperature does not get out of control. Secondly, these reactions tend to be oil-water two-phase or gas-liquid two-phase reaction, therefore good mass transfer is extremely important; Thirdly, organic peroxides are flammable, explosive and extremely unstable chemicals, thus the reaction is suggested to be completed in a short time to ensure the process safety. That is the purpose of ready to use and zero inventory, especially for some ultra-low temperature organic peroxides.

The general reaction formulas of the existing processes are as follows:

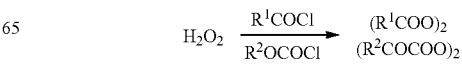

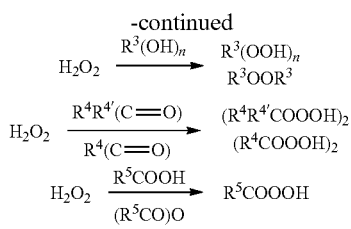

Where, $R^1$ is selected from $C_1$-$C_{20}$s saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl.

$R^2$ is selected from $C_1$-$C_{20}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl.

$R^3$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl.

$R^4$ or $R^{4'}$ is selected from $C_1$-$C_{12}$ saturated or unsaturated alkyl, unsubstituted or substituted aryl, unsubstituted or substituted heteroaryl, unsubstituted or substituted saturated heterocycloalkyl, unsubstituted or substituted partially saturated heterocycloalkyl, unsubstituted or substituted cycloalkyl.

$R^5$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated hetero-cycloalkyl, unsubstituted or substituted cycloalkyl.

Although a few continuous processes for the synthesis of organic peroxides have been developed, some challenges with the existing process are as follows: First, some of the continuous processes cannot complete the reaction in a short time, so it is necessary to use a delay line to extend the reaction time and increase the conversion rate, which results in a decrease in production efficiency. For example, Chinese patent CN104370789A disclosed a continuous process for the synthesis of bis(2-ethylhexyl) per-oxydicarbonate. It should be mentioned that three raw materials are firstly sent to the micro-reactor for reaction, and then extended into the pipeline for a complete reaction to obtain the products. The reaction time is about 4 to 9 min, which refers to the time required for the raw material to enter the reactor to the end of the reaction and obtain the crude product of the target product, but does not contain the workup time. Second, the scaling up effect is inevitable and brings a lot of uncertainty for further industrialization applications. For example, since the scaling up effect is uncertain and greatly affected by the scale of production, the process needs to be scaled up step by step for multiple times to industrialization, and it is necessary to readjust and optimize process conditions and parameters every time. Also, the scaling up effect would be involved when the production volume needs to be adjusted. Each adjustment of the production volume needs to readjust and optimize the process conditions and parameters, which would consume a lot of manpower and material resources and development time. The production volume would also be irregularly changed with the production scale due to the scaling up effect. However, in industrial production, even if the process conditions and parameters are adjusted in place, it is also needed to readjust and optimize the process conditions and parameters when the production scale is changed, thus the production process is lack of flexibility. Meanwhile, the stability and reliability of the process will be greatly affected by the uncertain scaling up effect, and the product quality may also be influenced by a small fluctuation in process conditions and parameters, making an unstable and uncontrollable product quality problem. In addition, these factors also bring potential safety risks to the production process.

The scaling up effect refers to the difference between the research results obtained by using small equipment for chemical process (i.e., small-scale) experiments (such as laboratory scale) and by using large-scale production facilities (such as industrial scale) under the same operating conditions. The main reason is that the temperature, concentration, and residence time distribution of materials in small-scale experimental equipment are different from those in large-scale equipment. In other words, it is impossible to repeat the research results of small-scale experiments on the industrial scale under the same operating conditions. It is necessary to adjust and optimize the process parameters and operating conditions to obtain the same or similar results on the industrial scale as small-scale experiments. For chemical engineering, the scaling up effect is a rough and urgent problem. If it is not solved, it will cause great uncertainty in the production process and product quality. First, it will directly cause the quality of downstream products to be unstable and difficult to control. Second, the uncertainty will cause the fluctuations of process parameters, which will lead to the inability to effectively control the production process, making the production safety impossible to be guaranteed, and laying many hidden dangers to the production process.

At the same time, the existing oxidation processes only produce the crude products of alkyl peroxide, dialkyl peroxide, peroxycarboxylic acid, diacyl peroxide, peroxydicarbonate, and peroxydiketal, which contain water, $H_2O_2$, salt and raw materials. Thus, these crude products need workup to get products that meet the market standards (For example, the requirements for commercially available tert-butyl hydroperoxide are as follows: di-tert-butyl peroxide $\leq 0.08$ wt. %, tert-butanol $\leq 0.5$ wt. %, other organic substances $\leq 0.4$ wt. %). The workup processes may be gas-liquid separation, pH adjustment, oil-water separation, vacuum distillation or distillation, flash separation, etc. For example, Chinese patent CN101298429 disclosed that a method to obtain the market standard tert-butyl hydroperoxide product by separating the reaction mixture and rectifying the oil phase with vacuum pressure. The existing workup process usually takes several hours with a long processing cycle and low efficiency and requires individual and dedicated equipment such as a rectifying column. In addition, since different organic peroxides need different workup processes, there is no universal equipment and process that can purify various alkyl peroxides, dialkyl peroxides, peroxycarboxylic acids, Diacyl peroxide compounds, peroxydicarbonates, and peroxydiketals in the existing processes.

Chinese patent CN101287704 disclosed a method for producing organic peroxides through micro-reaction technology.

Another Chinese patent CN101479239 disclosed another method for continuously preparing organic peroxides by using a plate heat exchanger with high heat exchange capacity. It can continuously prepare the selected organic peroxides at a given temperature by introducing different reactants at different positions (plates) of the plate heat exchanger. The reaction time on a laboratory scale ranges from 1 second to 45 seconds, but it will expand to 2 to 3 minutes on an industrial scale. Compared with batch processes, this continuous preparation method has certain advantages in production efficiency and safety. However, due to the unavoidable scaling-up effect, its industrial-scale reaction time is 2 to 180 times that of the laboratory scale, the significantly scaling-up effect (extend a wide range of reaction time from 2 to 180 times) has greatly increased the difficulty of industrialization.

In summary, there are many problems in the existing production process of organic peroxides: (1) Large quantities of organic peroxides (alkyl peroxides, dialkyl peroxides, peroxycarboxylic acids, diacyl peroxides, peroxydicarbonates and peroxydiketals) need to be purified, stored and transported, which makes the process have great safety risks; (2) It is not yet possible to achieve a continuous flow process that uses hydrogen peroxide, a catalyst, and an oxidized substrate as raw materials to directly obtain products that meet market standards. Therefore, the online manufacturing of the above organic peroxides in the true sense cannot be achieved, and the huge safety risks in oxide production and use cannot be fundamentally solved, and reduce production and use costs cannot be possible; (3) In addition, the existing processes have different degrees of scaling-up effects, which will consume a lot of manpower and material resources and leads to a lot of uncertainties when scaling up to industrialization. There are also problems with the reliability of the process after scaling up, which leads to unstable product quality and difficult control. Also, the production process is inflexible and has potential security risks; (4) The low reaction temperature results in the long production time and high production yield, and also reduces the production efficiency, which increases the difficulty for industrialization. What's more, the inability to achieve mass production limits its applications. Therefore, the development of a continuous flow production process has the advantages of simplicity, safety, efficiency, online production and easy to scale up is necessary and desired.

SUMMARY OF THE DISCLOSURE

In view of the shortcomings of the existing technologies, one technical problem to be solved in this disclosure is to propose an online continuous flow production process for directly preparing organic peroxides using hydrogen peroxide as raw materials. The organic peroxides are selected from alkyl peroxides, dialkyl peroxides, peroxycarboxylic acids, diacyl peroxides, peroxydicarbonates and peroxydiketals. The continuous flow production process provided in the disclosure effectively integrates the oxidation reaction and workup into one process. This process can efficiently and quickly produce organic peroxide products those meet the market standards. The production process overcomes the problems in the existing technologies, such as the scaling-up effect, long workup time, and the non-universal production process of different organic peroxides. Different types of organic peroxides can be produced by the same plug-and-produce integrated continuous flow reactor. The method in this disclosure can realize online manufacturing. The production and use of the organic peroxide products are performed simultaneously, namely the production process is seamlessly connected and synchronized with the downstream process (process using organic peroxide). So, the flexible manufacturing of organic peroxide products can be achieved including produce-to-use and ready-to-use production mode. This disclosure fundamentally solves the cost and safety issues of cold chain storage and transportation, and increase the yield and content of the produced organic peroxide products. This production process is easy to be industrialized and will greatly reduce the production cost and improve the safety of organic peroxides and downstream production.

In-situ production means that the manufacturers install the equipment to the location near or the same as the end consumer's location (or downstream user) for production, thereby greatly reducing a lot of intermediate links between the manufacturer with the end consumer (or downstream user), such as warehousing and logistics. In this way, it can save a lot of costs. However, in-situ production still cannot avoid the storage and transportation for a small number of products, for example, the transportation from one workshop to another in a factory, taking out products from production equipment for synthetic products, and transporting them to downstream production equipment. Online manufacturing, as a kind of in-situ production, refers to a production method in which production and usage of the products are performed simultaneously, seamlessly linked and synchronized with downstream processes, thereby achieve the flexible manufacturing of produce-to-use, ready-to-use. A plug-and-produce system is necessary to achieve online manufacturing. The so-called produce-to-use means that the production and consumption of the product are carried out simultaneously. The so-called ready-to-use means that the production can be carried out timely and on demand with zero inventory. The plug-and-produce system, that is, the product is obtained immediately after the production device is started, and it is produced on demand, and can be stopped at once when the demand is met. The time of online production can be shortened to equal to or less than ten minutes. It can be seamlessly connected with downstream users' production equipment and production processes, which fundamentally avoids the storage and transportation of products, saves costs and improves production. The safety also improves production efficiency. The production time refers to the time required for the raw materials to enter the reactor to meet the output of commercially available products, including reaction time and workup time, which is also called residence time in a continuous flow process. As a highly flexible production method, online manufacturing not only saves a lot of warehousing and logistics costs as other local production methods, but also effectively meets the fast, personalized and customized production needs. It also conforms to Industrialization 4.0 and the development direction of the fourth industrial revolution led by intelligent manufacturing.

In the present disclosure, the integrated continuous flow process and reactor for the systhesis of organic peroxide can be directly and seamlessly connected to the downstream end user's process and reactor, realizing produce to use, and it is even possible to achieve no accumulation of oxidized carboxylic acid esters, peroxycarbonates, or ketal peroxide. in the entire process. The integrated continuous flow process can be directly connected to polymerizers of polymer material synthesis, and vulcanizers in the film industry to form a fully continuous production and use of organic peroxides, which subvert the existing mode of production-storage-transport-storage-use. The production mode proposed in this disclosure realizes a produce-to-use, online manufacturing and ready-to-use of the synthesis of organic peroxides. For example, bis(2-ethylhexyl) peroxydicarbonate is one of the most important low temperature initiator components of PVC polymerization. The integrated continuous flow process of the present disclosure can be seamlessly connected with a PVC polymerization kettle. The bis(2-ethylhexyl) peroxydicarbonate, which meets the market standard, flows out from the integrated continuous flow reactor, then directly enter to the PVC polymerization kettle to participate in the polymerization reaction. The produce-to-use (without the accumulation and storage of organic peroxides), not only greatly improves the safety of the overall process, but also further reduces the production cost of the entire process, including downstream products.

EXPLANATION OF TERMS

The term "aryl" used in this patent refers to a full-carbon monocyclic or fused polycyclic group having 5 to 12 carbon atoms, which has a completely conjugated π electron system. Non-limiting examples of aromatic rings are: benzene ring, naphthalene ring and anthracene ring. The aromatic ring may be unsubstituted or substituted. The substituent of the aromatic ring is selected from halogen, nitro, amino, cyano, hydroxyl, $C_1$-$C_6$ alkyl, $C_1$-$C_6$ alkoxy, halo $C_1$-$C_6$ alkyl, halo $C_1$-$C_6$ alkoxy, $C_3$-$C_6$ cycloalkyl, halogenated $C_3$-$C_6$ cycloalkyl.

The term "heterocyclic aryl" used in this patent refers to an unsaturated carbocyclic ring having 5 to 12 ring atoms, in which one or more carbon atoms are replaced by heteroatoms such as N, O, S, et al. Heteroaryl rings can be monocyclic or bicyclic formed by two rings. The specific heterocyclic aromatic groups may be: pyridyl, pyrimidinyl, pyrazinyl, isoxazolyl, isothiazolyl, pyrazolyl, thiazolyl, oxazolyl, and imidazolyl. Heteroaryl groups can be unsubstituted or substituted. Heterocyclic aryl substituents are selected from halogen, nitro, amino, cyano, hydroxy, $C_1$-$C_6$ alkyl, $C_1$-$C_6$ alkoxy, halo $C_1$-$C_6$ alkyl, halo $C_1$-$C_6$ alkoxyl, $C_3$-$C_6$ cycloalkyl, halogenated $C_3$-$C_6$ cycloalkyl.

The term "heterocycloalkyl" used herein refers to a monocyclic or fused ring group having 5 to 12 ring atoms, in which one or two of which are selected from N, O, or S (O)m (where m is an integer from 0 to 2) and the remaining ring atoms are C. These rings can contain one or more double bonds, but do not have a completely conjugated π electron system. Examples of the unsubstituted heterocycloalkyl group include pyrrolidinyl, piperidinyl, piperazinyl, morpholino, thiomorpholino, homopiperazinyl, et al. The heterocyclic ring may be unsubstituted or substituted. Heterocyclic substituents are selected from halogen, nitro, amino, cyano, hydroxyl, $C_1$-$C_6$ alkyl, $C_1$-$C_6$ alkoxy, halo $C_1$-$C_6$ alkyl, halo $C_1$-$C_6$ alkoxy, $C_3$-$C_6$ cycloalkyl, halogenated $C_3$-$C_6$ cycloalkyl.

The term "cycloalkyl" used herein refers to a saturated monocyclic carbocyclic ring having 3 to 12 carbon atoms, unless a different number of atoms is indicated. Cycloalkyl includes cyclopropyl, cyclobutyl, cyclopentyl, cyclohexyl, cycloheptyl, and cyclooctyl, et al. The cycloalkyl group can be unsubstituted or substituted. Cycloalkyl can also be optionally substituted on any available carbon with one or more substituents selected from the group consisting of alkoxy, halogen, haloalkyl, such as perfluoroalkyl.

The term "alkoxy" refers to —O-alkyl groups. Examples of "alkoxy" in this patent include, but not limited to methoxy, ethoxy, n-propoxy, isopropyl, n-butoxy and tert-butoxy. "Alkoxy" also includes substituted alkoxy. The alkoxy group may be optionally substituted with one or more halogen atoms.

The term "alkyl" as used herein includes both straight-chain and branched-chain alkyl groups. When referring to a single alkyl group such as "propyl", it only refers to a straight-chain alkyl group. When referring to a single branched alkyl group such as "isopropyl", it only refers to a branched alkyl group. For example, "$C_1$-$C_6$ alkyl" includes $C_1$-$C_4$ alkyl, $C_1$-$C_3$ alkyl, methyl, ethyl, n-propyl, isopropyl, and tert-butyl.

Continuous process refers to a continuous exchange of materials between the production system and the outside system during the production process. During the whole process, raw materials are continuously entered to the system and products are continuously produced. Continuous-flow process is a type of continuous process, in which raw materials are continuously added to produce products and products are carried out continuously. There is no "stand" in the process, and is a "pipeline" chemical production process. When the process operation reaches a steady state, the state parameters such as the composition and temperature of the materials at any position in the reactor do not change with time. It is a steady state process, so the production process and product quality are stable.

In a process that includes multiple steps, if some of the steps are continuous, the process can be called a continuous process. However, only all steps in a process are continuous, that is, continuous input of raw materials continuous output of product, this process can be called a continuous flow process.

In order to solve the technical problem, this disclosure innovatively provides a continuous flow production process for directly preparing organic peroxides by using hydrogen peroxide, a catalyst, and an oxidation substrate. The production process uses hydrogen peroxide, a catalyst, and an oxidizing substrate as the starting reaction materials, and successively performs the oxidation process and workup to obtain an organic peroxide.

The production process is performed in a plug-and-produce integrated continuous flow reactor, and the hydrogen peroxide, catalyst and oxidation substrate continuously enter a feed port and the target product organic peroxide is continuously obtained at the reactor outlet. Moreover, the production process has no scaling-up effect, the catalyst is an acid or a base, and the organic peroxide is any one selected from the group consisting of alkyl peroxides, dialkyl peroxides, peroxycarboxylic acids, and diacyl peroxides, peroxydicarbonate, peroxydiketal; the oxidized substrate is selected from alcohols, carboxylic acids, anhydrides, ketones, acid chlorides, and chloroformates. Based on the advantages of the integrated reaction process and the plug-and-produce integrated continuous flow reactor, the present disclosure completely improves the existing processes for producing organic peroxides, which is able to realize online continuous flow production of organic peroxides, and effectively integrate the oxidation process and workup process. This process quickly (within 6 minutes) produces organic peroxide products that meet commercial standards. The production process does not have the limitations, such as the scaling-up effect, long-time workup, and lacking the universality for different organic peroxides, and achieve the production of different organic peroxides on the same plug-and-produce integrated continuous flow reactor.

In particular, the production process in this disclosure can realize the production and use of organic peroxide products simultaneously, and can be seamlessly connected and synchronized with downstream processes (processes using organic peroxides) to fundamentally solve the high cost and safety issues of cold chain storage and transportation of the organic peroxides industry. In addition, this process can achieve high yield and content organic peroxide products, that is easy to be mass-produced and greatly reduce the production cost and improve the production safety of organic peroxide production and downstream.

The general route of the present disclosure is as follows:

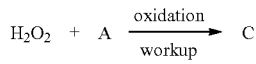

wherein A is an oxidation substrate, including alcohol, carboxylic acid, anhydride, ketone, acid chloride and chloroformate; C is alkyl peroxide, dialkyl peroxide, peroxycarboxylic acid, diacyl peroxide, peroxydicarbonate and peroxydiketal.

In some embodiments, when A is an acid chloride, the general formula is $R^1COCl$; when A is a chloroformate, the general formula is $R^2OCOCl$; when A is an alcohol, the general formula is $R^3(OH)n$, where n=1, 2, 3 . . . ; When A is ketone, the general formula is $R^4R^{4'}(CO)$ or $R^4(CO)$ (Cyclone); when A is carboxylic acid, the general formula is $R^5COOH$; when A is carboxylic anhydride, the general formula is $(R^5CO)_2OR^5(CO)_2O$(anhydride).

When C is a diacyl peroxide, the general formula is $R^1(COO)_2$; when C is a peroxydicarbonate, the general formula is $R^2(OCOO)_2$; when C is an alkyl peroxide, the general formula is $R^3(OOH)_n$, where n=1, 2, 3 . . . ; the general formula when C is a dialkyl peroxide is $R^3OOR_3$, where n=1; the general formula when C is a diketyl peroxide is $R^4(OOOH)_2$; when C is a peroxycarboxylic acid, the general formula is $R^5OOOH$;

$R^1$ is selected from $C_1$-$C_{20}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl;

$R^2$ is selected from $C_1$-$C_{20}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl;

$R^3$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl;

$R^4$ or $R^{4'}$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl.

$R^5$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl.

In some embodiments, $R^1$ is selected from $C_1$-$C_{18}$ saturated or unsaturated alkyl group, an unsubstituted or substituted aryl group, an unsubstituted or substituted heterocyclic aryl group, an unsubstituted or substituted saturated heterocycloalkyl, unsubstituted or substituted partially saturated heterocycloalkyl, unsubstituted or substituted cycloalkyl.

$R^2$ is selected from methyl, ethyl, propyl, isopropyl, butyl, sec-butyl, 2-ethylpentyl, isotridecyl, heptadecyl, cyclohexyl-1, 4-tert-butylcyclohexyl, benzyl, phenoxyethyl.

$R^3$ is selected from the group consisting of tert-butyl, tert-pentyl, 2,4,4-trimethyl-2-pentyl, and 2,5-dimethylhexyl.

$R^4$ or $R^{4'}$ is more selected from methyl, ethyl, isobutyl, 2-oxopropyl, —(CH2)5-.

$R^5$ is selected from methyl and ethyl.

In some embodiments, $R^1COC^1$ is selected from acetyl chloride, propionyl chloride, butyryl chloride, isobutyryl chloride, valeryl chloride, 2-methylbutyryl chloride, pivaloyl chloride, 2-methylvaleryl chloride, 2-ethylbutyryl chloride, 2-ethyl Hexanoyl chloride, nonanoyl chloride, 2,4,4-trimethylvaleryl chloride, 3,5,5-trimethylhexanoyl chloride, neodecanoyl chloride, decanoyl chloride, lauroyl chloride, benzoyl chloride, 2-methylbenzoyl chloride, 4-methylbenzoyl chloride, 4-chlorobenzoyl chloride, 2,4-dichlorobenzoyl chloride, naphthoyl chloride.

$R^2OCOCl$ is selected from methyl chloroformate, ethyl chloroformate, n-propyl chloroformate, isopropyl chloroformate, n-butyl chloroformate, sec-butyl chloroformate, 2-ethylhexyl chloroformate, and isodecyl chloroformate. Trialkyl esters, stearyl chloroformate, cyclohexyl chloroformate, 4-tert-butylcyclohexyl chloroformate, benzyl chloroformate, 2-phenoxyethyl chloroformate.

$R_3(OH)n$ is selected from tert-butanol, tert-amyl alcohol, 2,4,4-trimethyl-2-pentanol, 2,5-dimethyl-2,5 dihydroxyhexane.

$R^4R^{4'}(CO)$ is selected from methyl ethyl ketone, methyl isobutyl ketone and acetylacetone; $R^4(CO)$ is further selected from cyclohexanone.

$R^5COOH$ is selected from acetic acid and propionic acid.

$(R^5CO)_2O$ is selected from acetic anhydride and propionic anhydride.

The CAS Numbers are as follows: diisobutyrylperoxide: 3437-84-1, bis(3-methoxybutyl) peroxydicarbonate: 52238-68-3, bis(ethoxyhexane) ester): 763-69-9, diisopropyl peroxide dicarbonate: 105-64-6, dibutyl peroxide dicarbonate: 16215-49-9, di (3,5,5-trimethylhexanoyl) peroxide: 3851-87-4, bis(2-ethylhexyl) peroxydicarbonate: 16111-62-9, methyl ethyl ketone peroxide: 1338-23-4, acetylacetone peroxide: 37187-22-7, methyl isobutyl ketone peroxide: 37206-20-5, tert-butyl hydroperoxide: 75-91-2, di-tert-butyl peroxide: 110-05-4, tert-amyl hydroperoxide: 3425-61-4, di-tert-amyl peroxide: 10508-09-5, peracetic acid: 79-21-0, 1,1,3,3-tetramethylbutyl hydroperoxide: 5809-08-5.

In some embodiments, when an alkyl peroxide or a dialkyl peroxide is produced, the oxidation substrate is an alcohol; a peroxycarboxylic acid is produced when the oxidation substrate is carboxylic acid; diacyl peroxide is produced when the substrate is acid chloride; peroxydicarbonate is produced when the substrate is chloroformate; diketalperoxide is produced when the oxidized substrate is ketone.

The solution of the present disclosure uses hydrogen peroxide, a catalyst, and an oxidationsubstrate as starting materials, which achieves the target of "ready-to-use production" and avoids the safety problems of storing a large number of products. Also, there is no scaling-up effect in this process, which greatly reduces the difficulty for industrial application. When it is scaled up to industrialization, it can be scaled up to the required production scale at once without the tedious and complicated scale-up step-by-step, or adjustment and optimization of process conditions and parameters, which greatly saves manpower and material resources and project development time. In industrialization, the production scale can be changed flexibly without readjusting and optimizing process conditions and parameters, and the production process is flexible; no scaling-up effect makes the production process stable and reliable, fluctuations in process conditions and parameters will not affect product quality and the product quality is easy to control, which is also greatly improves the safety of the production process.

The production process of the disclosure can quickly continuously complete a multi-step reaction for preparing organic peroxides at high temperatures. With the utilization the division of functional unit temperature zones, optimization of the temperature settings and the synergistic effect of functional units, the production time can be shortened to 6 minutes, which greatly improves the process efficiency. It can be seen that the production process in this disclosure breaks through the limitations of the existing technologies. With the harsh and dangerous conditions that cannot be achieved by the existing technologies, this disclosure achieves high-efficiency and high-quality and without scaling-up effect synthesis of organic peroxides, which is extremely suitable for industrial application and a major break-through in this field.

The continuous flow process of the present disclosure can realize the ready-to-use production, avoiding the hidden dangers of storing organic peroxide products. Also, the product quality is stable and reproducible due to the great stability and reliability of this process. It also solves the problems of the scaling-up effect in the industrialization of the organic peroxide continuous flow process. At the same time, the plug-and-produce integrated continuous flow reactor requires no delay pipeline, which has the advantages of short reaction time, small volume, small footprint. In this way, this process greatly saves the workshop land and improve production efficiency.

In some embodiments, the production time in this disclosure is equal to or less than 6 min. Preferably, the production time is 1 to 6 min. More preferably, the production time is 2 to 5 min. More preferably, the production time is 3 to 4 min. The production time refers to the time required for the reaction raw materials (reaction substrate, oxidant, and condensing agent) to enter the integrated continuous flow reactor to produce a target product that meets the commercially available standards, including the oxidation process time and workup time.

The target product organic peroxide produced by the process in this disclosure is a product that meets the standards for commercia application.

In some embodiments, the target product organic peroxide is selected from the group consisting of diacyl peroxide and dicarbonate peroxide, and the content of chloride ion in the organic peroxide is ≤0.05 wt. %, and the content of $H_2O_2$ is ≤0.1 wt. %.

In some embodiments, the organic peroxide of the target product is selected from alkyl peroxides, and the content of $H_2O_2$ and di-t-butyl hydroperoxide in the alkyl peroxide is ≤0.1 wt. %.

In some embodiments, the organic peroxide of the target product is selected from the group consisting of a dialkyl peroxide, a peroxycarboxylic acid, and a diketal peroxide, and the $H_2O_2$ content in the organic peroxide of the target product is ≤0.1 wt. %.

In some embodiments, the temperature of the oxidation process is 0 to 110° C. Preferably 20 to 100° C. More preferably 30 to 90° C. More preferably 50 to 80° C. More preferably 60 to 70° C.

In some embodiments, the temperature of the workup process is 0 to 50° C., preferably 0 to 40° C., more preferably 5 to 30° C., more preferably 5 to 20° C., more preferably 5 to 10° C.

In some embodiments, the yield of the organic peroxide is ≥71%; preferably, ≥85%; preferably, ≥94%.

In some embodiments, the content of the organic peroxide is ≥79%; preferably, ≥86%; preferably, ≥96%.

In some embodiments, the base is selected any one from water-soluble metal hydroxides, water-soluble quaternary ammonium hydroxides, water-soluble tertiary amines, water-soluble metal carbonates or water-soluble metal phosphates, preferably alkali metal hydroxides, water-soluble metal carbonate or alkaline earth metal hydroxide is more preferably lithium hydroxide, sodium hydroxide, potassium hydroxide, sodium carbonate, or potassium carbonate.

In some embodiments, the mass concentration of the lye is 5 wt. % to 45 wt. %, preferably 15 wt. % to 35 wt. %, and preferably 20 wt. % to 30 wt. %.

In some embodiments, the acid is selected from all known organic and inorganic acids, preferably sulfuric acid, phosphoric acid, and trifluoroacetic acid.

In some embodiments, the mass concentration of the acid solution is 50 wt. % to 90 wt. %, preferably 60 wt. % to 80 wt. %, and preferably 70 wt. % to 80 wt. %.

In some embodiments, the hydrogen peroxide concentration is preferably 30 wt. % to 50 wt. %.

In some embodiments, the molar ratio of the acid to the oxidized substrate is 0.5:1 to 1.1:1, preferably 0.6:1 to 1:1, and more preferably 0.7:1 to 0.9:1.

In some embodiments, the molar ratio of hydrogen peroxide to oxidized substrate is 0.5:1 to 2.5:1, preferably 0.6:1 to 2:1, more preferably 0.7:1 to 1.15:1, and still more preferably 0.8:1 to 1.05:1.

In some embodiments, the molar ratio of the base to the oxidized substrate is 1:1 to 1.4:1, preferably 1.1:1 to 1.3:1, and more preferably 1.15:1 to 1.2:1.

In some embodiments, the acid liquid flow rate is 0.03 to 5 L/h, preferably 0.03 to 4 L/h, and more preferably 0.03 to 3 L/h.

In some embodiments, the flow rate of the lye is 1 to 5 L/h, preferably 1.5 to 4 L/h, and more preferably 1.8 to 2.5 L/h.

In some embodiments, the flow rate of hydrogen peroxide is 0.3 to 4 L/h, preferably 0.3 to 3 L/h, and more preferably 0.3 to 2 L/h.

In some embodiments, the flow rate of the oxidized substrate is 1 to 5 L/h, preferably 1.5 to 4 L/h, and more preferably 2 to 3 L/h.

In some embodiments, the organic peroxide is tert-butyl hydroperoxide, the oxidation substrate is tert-butanol, and the catalyst is an acid, wherein:

The hydrogen peroxide concentration is 30 wt. % to 50 wt. %.

The temperature of the oxidation process is 0 to 110° C., preferably 20 to 100° C., more preferably 30 to 90° C., more preferably 50 to 80° C., and still more preferably 60 to 70° C.

The temperature of the workup process is 0 to 50° C., preferably 0 to 40° C., preferably 5 to 30° C., preferably 5 to 20° C., preferably 5 to 10° C.

The production time of the continuous flow process is ≤4 min, preferably, the production time is 1 to 3 min; more preferably, the production time is 2 to 3 min.

The yield of the t-butyl hydrogen peroxide is ≥71%; preferably, ≥81%.

The content of the t-butyl hydroperoxide is ≥80%; preferably, ≥84%.

The content of other organic peroxide impurities ($H_2O_2$ and di-tert-butyl hydroperoxide) in the t-butyl hydroperoxide is 0.05 to 0.08 wt. %.

The acid is any one selected from all known organic and inorganic acids, preferably sulfuric acid, phosphoric acid, trifluoroacetic acid.

The mass concentration of the acid solution is 50 wt. % to 90 wt. %, preferably 60 wt. % to 80 wt. %, preferably 70 wt. % to 80 wt. %.

The acid liquid flow rate is 1 to 3 L/h, preferably 1.5 to 2.5 L/h, preferably 1.5 to 2 L/h.

The flow rate of the hydrogen peroxide is 1 to 3 L/h, preferably 1.5 to 2.5 L/h, preferably 1.5 to 2 L/h.

The t-butanol flow rate is 1 to 4 L/h, preferably 1.5 to 3 L/h, and more preferably 2 to 3 L/h.

The molar ratio of the acid to tert-butanol is 0.5:1 to 1:1, preferably 0.5:1 to 0.9:1, preferably 0.5:1 to 0.7:1, preferably 0.5:1 to 0.6:1.

The molar ratio of the hydrogen peroxide to tert-butanol is 0.8:1 to 1.2:1, preferably 0.9:1 to 1.1:1, preferably 0.9:1 to 1.05:1.

In some embodiments, the organic peroxide is tert-amyl hydroperoxide, the oxidation substrate is tert-amyl alcohol, and the catalyst is an acid, among which, preferably:

The hydrogen peroxide concentration is 30% to 50%.

The temperature of the oxidation process is 0 to 110° C., preferably 20 to 100° C., more preferably 30 to 90° C., more preferably 50 to 80° C., and still more preferably 60 to 70° C.

The temperature of the workup process is 0 to 50° C., preferably 0 to 40° C., preferably 5 to 30° C., preferably 5 to 20° C., preferably 5 to 10° C.

The production time of the continuous flow process is ≤4 min, preferably, the production time is 1 to 3 min; more preferably, the production time is 2 to 3 min.

The yield of the tert-amyl hydrogen peroxide is ≥73%; preferably, ≥79%.

The content of the t-amyl hydroperoxide is ≥83.9%; preferably, ≥84%.

The content of $H_2O_2$ in the tert-amyl hydrogen peroxide is 0.05 to 0.08 wt. %.

The acid is any one selected from all known organic and inorganic acids, preferably sulfuric acid, phosphoric acid, trifluoroacetic acid.

The mass concentration of the acid solution is 50 wt. % to 90 wt. %, preferably 60 wt. % to 80 wt. %, and more preferably 70 wt. % to 80 wt. %.

The acid liquid flow rate is 1 to 3 L/h, preferably 1.5 to 2.5 L/h, preferably 1.5 to 2 L/h.

The flow rate of the hydrogen peroxide is 1 to 3 L/h, preferably 1.5 to 2.5 L/h, preferably 1.5 to 2 L/h.

The t-amyl alcohol flow rate is 1 to 4 L/h, preferably 1.5 to 3 L/h, and more preferably 2 to 3 L/h.

The molar ratio of the acid to tert-amyl alcohol is 0.8:1 to 1.1:1, preferably 0.9:1 to 1:1, and more preferably 0.95:1 to 1:1.

The molar ratio of the hydrogen peroxide to tert-amyl alcohol is 0.9:1 to 1.3:1, preferably 1:1 to 1.25:1, and more preferably 1.14:1 to 1.2:1.

In some embodiments, the organic peroxide is bis(3,5,5-trimethylhexanoyl) peroxide, the oxidation substrate is 3,5,5-trimethylhexanoyl chloride, the catalyst is a base. Among them, preferably:

The hydrogen peroxide concentration is 30 wt. % to 50 wt. %.

The temperature of the oxidation process is 0 to 110° C., preferably 20 to 100° C., preferably 30 to 90° C., preferably 50 to 80° C., preferably 60 to 70° C.

The temperature of the workup process is 0 to 50° C., preferably 0 to 40° C., preferably 5 to 30° C., preferably 5 to 20° C., preferably 5 to 10° C.

The production time of the continuous flow process is ≤4 min, preferably, the production time is 1 to 3 min; preferably, the production time is 2 to 3 min.

The yield of the bis(3,5,5-trimethylhexanoyl) peroxide is ≥91%; preferably, ≥92%.

The content of the bis(3,5,5-trimethylhexanoyl) peroxide is ≥91%; preferably, ≥93%.

The target product bis(3,5,5-trimethylhexanoyl) peroxide has a chloride ion content of 0.02 wt. % to 0.05 wt. %, and a $H_2O_2$ content of 0.05 to 0.1 wt. %.

The base is any one selected from water-soluble metal hydroxide, water-soluble quaternary ammonium hydroxide, water-soluble tertiary amine, water-soluble metal carbonate or water-soluble metal phosphate, preferably alkali metal hydroxide, water-soluble metal carbonic acid Salt or alkaline earth metal hydroxide, more preferably lithium hydroxide, sodium hydroxide, potassium hydroxide, sodium carbonate, potassium carbonate.

The lye mass concentration is 5 wt. % to 45 wt. %, preferably 15 wt. % to 35 wt. %, and more preferably 20 wt. % to 30 wt. %.

The lye flow rate is 1 to 4 L/h, preferably 1.5 to 3 L/h, and more preferably 1.8 to 2.5 L/h. The hydrogen peroxide flow rate is 0.3 to 1 L/h, preferably 0.5 to 0.8 L/h, preferably 0.6 to 0.7 L/h.

The flow rate of the 3,5,5-trimethylhexanoyl chloride is 1 to 3 L/h, preferably 1.5 to 2.5 L/h, and more preferably 1.5 to 2 L/h.

The molar ratio of the hydrogen peroxide to 3,5,5-trimethylhexanoyl chloride is 0.5:1 to 0.8:1, preferably 0.55:1 to 0.75:1, preferably 0.6:1 to 0.7:1.

The molar ratio of the base and 3,5,5-trimethylhexanoyl chloride is 1:1 to 1.4:1, preferably 1.1:1 to 1.3:1, preferably 1.15:1 to 1.2:1.

In some embodiments, the organic peroxide is bis(2-ethylhexyl) dicarbonate, the oxidation substrate is -2ethylhexyl chloroformate, and the catalyst is a base, among which, preferably:

The mass concentration of hydrogen peroxide is 30 wt. % to 50 wt. %.

The temperature of the oxidation process is 0 to 110° C., preferably 20 to 100° C., preferably 30 to 90° C., preferably 50 to 80° C., preferably 60 to 70° C.

The temperature of the workup process is 0 to 50° C., preferably 0 to 40° C., preferably 5 to 30° C., preferably 5 to 20° C., preferably 5 to 10° C.

The production time of the continuous flow process is ≤4 min, preferably, the production time is 1 to 3 min; more preferably, the production time is 2 to 3 min.

The yield of the bis(2-ethylhexyl) peroxydicarbonate is ≥86.5%; preferably, the yield of the bis(2-ethylhexyl) peroxydicarbonate is ≥90%.

The content of the bis(2-ethylhexyl) peroxydicarbonate is ≥95%; preferably, the content of the bis(2-ethylhexyl) peroxydicarbonate is ≥96%.

The target product has a chloride ion content of bis(2-ethylhexyl dicarbonate) of 0.02 wt. % to 0.05 wt. % and a content of $H_2O_2$ of 0.05 wt. % to 0.1 wt. %.

The base can be water-soluble metal hydroxide, water-soluble quaternary ammonium hydroxide, water-soluble tertiary amine, water-soluble metal carbonate or water-soluble metal phosphate, preferably alkali metal hydroxide, water-soluble metal carbonate Salt or alkaline earth metal hydroxide, more preferably sodium hydroxide, potassium hydroxide, sodium carbonate, potassium carbonate or lithium hydroxide.

The mass concentration of the lye is 5 wt. % to 45 wt. %, preferably 15 wt. % to 35 wt. %, and more preferably 20 wt. % to 30 wt. %.

The flow rate of the lye is 1 to 4 L/h, preferably 1.5 to 3 L/h, preferably 1.8 to 2.5 L/h.

The hydrogen peroxide flow rate is 0.3 to 1 L/h, preferably 0.5 to 0.8 L/h, preferably 0.6 to 0.7 L/h.

The flow rate of the 2-ethylhexyl chloroformate is 1 to 3 L/h, preferably 1.5 to 2.5 L/h, and more preferably 1.5 to 2 L/h.

The molar ratio of the hydrogen peroxide to 2-ethylhexyl chloroformate is 0.5:1 to 0.8:1, preferably 0.55:1 to 0.75:1, and more preferably 0.6:1 to 0.7:1.

The molar ratio of the base and 2-ethylhexyl chloroformate is 1:1 to 1.4:1, preferably 1.1:1 to 1.3:1, and more preferably 1.15:1 to 1.2:1.

It should be noted that the mass concentration of hydrogen peroxide, catalyst and oxidized substrate used in actual production (including laboratory, pilot test, and actual production process) will have a deviation of ±2 percentage points; the temperature in the temperature zone will have Deviation of ±3° C.; production time will have a deviation of ±5 s.

In order to satisfy the conditions of continuous flow process, the present disclosure has developed a special integrated reactor. The reactor as a modular structure, and it is necessary to design the organization method, number of modules, and the modules of each temperature zone. It is also necessary to develop targeted process conditions and parameters, including the division and temperature setting of each temperature zone. The synergistic effects of the above factors make this continuous flow process possible. In addition, the temperature can be further combined with the material concentration, the material ratio, and the material flow rate to match the reaction process and obtain better reaction results. The materials include raw materials, intermediate products in the reaction process, the material concentrations include the concentrations of raw materials and the concentrations of intermediate products, and the material ratios include each raw material ratio and each intermediate product concentration, the material flow rates include the flow rate of each raw material and the flow rate of each intermediate product.

In some embodiments, in order to match the continuous flow production process of organic peroxide, the plug-and-produce integrated continuous flow reactor adopts a unitized structure, including an oxidation unit and a workup unit, wherein: The oxidation unit is used for the reaction to form alkyl peroxide, dialkyl peroxide, peroxycarboxylic acid, diacyl peroxide, peroxydicarbonate and peroxydiketal, with hydrogen peroxide, catalyst and oxidation substrate. The workup unit is used for workup of alkyl peroxide, dialkyl peroxide, peroxycarboxylic acid, diacyl peroxide, peroxydicarbonate, and peroxydiketal.

In some embodiments, the temperature of the oxidation unit is 0 to 110° C., preferably 20 to 100° C., more preferably 30 to 90° C., more preferably 50 to 80° C., and still more preferably 60 to 70° C.

In some embodiments, the temperature of the workup unit is 0 to 50° C., preferably 0 to 40° C., more preferably 5 to 30° C., more preferably 5 to 20° C., and even more preferably 5 to 10° C.

In some embodiments, in order to match the continuous flow production process of organic peroxides, the plug-and-produce integrated continuous flow reactor adopts a unitized structure, and each of the units independently contains more than one reactor module or reactor module group, wherein the reactor module group is composed of multiple reactor modules connected in series or in parallel, and each unit is connected in series with each other.

In some embodiments, in order to match the continuous flow production process of organic peroxides, the plug and play integrated continuous flow reactor adopts a unitized structure, and each of the units includes at least one temperature zone, Each temperature zone independently includes more than one reactor module or reactor module group, wherein the reactor module group is composed of multiple reactor modules connected in series or in parallel, and each temperature zone is connected in series with each other.

In some embodiments, the units further include a buffer vessel. The buffer is a container with a certain volume, which is mainly used to buffer pressure fluctuations and balance flow differences of the system, so that the system works more smoothly.

In some embodiments, the number of feed ports of the plug-and-produce integrated continuous flow reactor is one or more, and the number of feed ports of the plug-and-produce integrated continuous flow reactor is one or more.

In some embodiments, the reactor module is optionally any type of reactor capable of realizing a continuous flow process, and the reactor is any one or more selected from a microreactor, a Tandem loop reactor, and a tube reactor. The micro-reactor, also known as a micro-structure reactor or a micro-channel reactor, is a device in which chemical reactions occur in a limited area with a generally lateral dimension of 1 mm and below. The micronized channel is the most typical form of the limited areas.

The series coil reactor, that is, a reactor composed of a series of coil reactors connected in series by a pipe, in which the coil reactor is a tubular reactor in coil form. Tubular reactor is a kind of continuous operation reactor with tubular shape and large aspect ratio, which firstly appeared in the middle of the last century. This type of reactor can be very long; it can be a single tube or multiple tubes in parallel; it also can be empty or filled.

In some embodiments, the reactor may be one or more.

In some embodiments, the materials of the reactor channel include the single crystal silicon, special glass, ceramic, stainless steel or metal alloy with a corrosion-resistant coating, and polytetrafluoroethylene.

In some embodiments, the reactor modules, the reactor module groups, the reactor modules and the reactor module groups are all connected in series or in parallel, respectively.

In some embodiments, the continuous flow production process is performed in a plug-and-produce integrated continuous flow reactor including 4 temperature zones.

In some embodiments, the continuous flow production process is performed in a plug-and-produce integrated continuous flow reactor, which include 4 temperature zones.

In some embodiments, the continuous flow production process oxidation unit includes three temperature zones, namely temperature zone 1, temperature zone 2 and temperature zone 3, and the workup unit includes one temperature zone, which is temperature zone 4.

In some embodiments, the continuous flow production process includes the following steps:

(a) The hydrogen peroxide, catalyst, and oxidized substrate are transported into the oxidation unit, and pass through temperature zone 1 to temperature zone 3 in sequence, and the corresponding alkyl peroxide, dialkyl peroxide, peroxycarboxylic acid, and diacyl peroxide are completely reacted Compounds, peroxydicarbonates and peroxydiketals.

(b) The reaction liquid flows out from the temperature zone 3, then enters the workup unit, and is sequentially processed through the temperature zone 4 to obtain the final product.

In some embodiments, the temperature in the temperature zone 1 is 0 to 60° C., preferably 0 to 40° C., more preferably 5 to 30° C., more preferably 5 to 20° C., and even more preferably 5 to 10° C.

In some embodiments, the temperature in the temperature zone 2 is 30 to 110° C., preferably 40 to 100° C., more preferably 50 to 90° C., more preferably 60 to 80° C., and more preferably 65 to 70° C.

In some embodiments, the temperature in the temperature zone 3 is 0 to 50° C., preferably 0 to 40° C., more preferably 5 to 30° C., more preferably 5 to 20° C., and even more preferably 5 to 10° C.

In some embodiments, the temperature in the temperature zone 4 is 0 to 50° C., preferably 0 to 40° C., more preferably 5 to 30° C., more preferably 5 to 20° C., and even more preferably 5 to 10° C.

In some embodiments, when the organic peroxide is t-butyl hydroperoxide, the oxidation substrate is t-butanol, and the catalyst is an acid. Among them, preferably:

The temperature in the temperature zone 1 is 0 to 40° C., preferably 5 to 30° C., more preferably 5 to 20° C., and even more preferably 5 to 10° C.

The temperature in the temperature zone 2 is 40 to 100° C., preferably 50 to 90° C., more preferably 60 to 85° C., and more preferably 70 to 80° C.

The temperature in the temperature zone 3 is 0 to 40° C., more preferably 5 to 30° C., more preferably 5 to 20° C., and still more preferably 5 to 10° C.

The temperature in the temperature zone 4 is 0 to 40° C., more preferably 5 to 30° C., more preferably 5 to 20° C., and still more preferably 5 to 10° C.

The yield of the t-butyl hydrogen peroxide is ≥71%; preferably, the yield of the t-butyl hydrogen peroxide is ≥81%.

The content of the t-butyl hydroperoxide is ≥80%; preferably, the content of the t-butyl hydroperoxide is ≥84%.

The content of other organic peroxide impurities ($H_2O_2$ and di-tert-butyl hydroperoxide) in the t-butyl hydroperoxide is 0.05 wt. % to 0.08 wt. %.

The hydrogen peroxide concentration is 30 wt. % to 50 wt. %.

The acid is selected from all known organic and inorganic acids, preferably sulfuric acid, phosphoric acid, trifluoroacetic acid.

The mass concentration of the acid solution is 50 wt. % to 90 wt. %, preferably 60 wt. % to 80 wt. %, and more preferably 70 wt. % to 80 wt. %.

The acid liquid flow rate is 1 to 3 L/h, preferably 1.5 to 2.5 L/h, and more preferably 1.5 to 2 L/h.

The flow rate of the hydrogen peroxide is 1 to 3 L/h, preferably 1.5 to 2.5 L/h, and more preferably 1.5 to 2 L/h.

The t-butanol flow rate is 1 to 4 L/h, preferably 1.5 to 3 L/h, and more preferably 2 to 3 L/h.

The molar ratio of the acid to tert-butanol is 0.5:1 to 1:1, preferably 0.5:1 to 0.9:1, more preferably 0.5:1 to 0.7:1, and still more preferably 0.5:1 to 0.6:1.

The molar ratio of the hydrogen peroxide to tert-butanol is 0.8:1 to 1.2:1, preferably 0.9:1 to 1.1:1, and more preferably 0.9:1 to 1.05:1.

In some embodiments, when the organic peroxide is tert-amyl hydroperoxide, the oxidation substrate is tert-amyl alcohol, and the catalyst is an acid. Among them, preferably:

The temperature in the temperature zone 1 is 0 to 40° C., preferably 5 to 30° C., more preferably 5 to 20° C., and even more preferably 5 to 10° C.

The temperature in the temperature zone 2 is 40 to 100° C., preferably 50 to 90° C., more preferably 60 to 85° C., and more preferably 70 to 80° C.

The temperature in the temperature zone 3 is 0 to 40° C., more preferably 5 to 30° C., more preferably 5 to 20° C., and still more preferably 5 to 10° C.

The temperature in the temperature zone 4 is 0 to 40° C., more preferably 5 to 30° C., more preferably 5 to 20° C., and still more preferably 5 to 10° C.

The yield of the tert-amyl hydrogen peroxide is ≥73%; preferably, the yield of the tert-amyl hydrogen peroxide is ≥79%.

The content of the t-amyl hydroperoxide is ≥83.9%; preferably, the content of the t-amyl hydroperoxide is ≥84%.

The content of $H_2O_2$ in the t-butyl hydroperoxide is 0.05 wt. % to 0.08 wt. %.

The mass concentration of hydrogen peroxide is 30 wt. % to 50 wt. %.

The acid is selected from all known organic and inorganic acids, preferably sulfuric acid, phosphoric acid, trifluoroacetic acid.

The mass concentration of the acid solution is 50 wt. % to 90 wt. %, preferably 60 wt. % to 80 wt. %, and more preferably 70 wt. % to 80 wt. %.

The acid liquid flow rate is 1 to 3 L/h, preferably 1.5 to 2.5 L/h, and more preferably 1.5 to 2 L/h.

The flow rate of the hydrogen peroxide is 1 to 3 L/h, preferably 1.5 to 2.5 L/h, and more preferably 1.5 to 2 L/h.

The t-amyl alcohol flow rate is 1 to 4 L/h, preferably 1.5 to 3 L/h, and more preferably 2 to 3 L/h.

The molar ratio of the acid to tert-amyl alcohol is 0.8:1 to 1.1:1, preferably 0.9:1 to 1:1, and more preferably 0.95:1 to 1:1.

The molar ratio of the hydrogen peroxide to tert-amyl alcohol is 0.9:1 to 1.3:1, preferably 1:1 to 1.25:1, and more preferably 1.14:1 to 1.2:1.

In some embodiments, when the organic peroxide is bis(3,5,5-trimethylhexanoyl) peroxide, the oxidation substrate is 3,5,5-trimethylhexanoyl chloride, and the catalyst Is a base, of which, preferably:

The temperature in the temperature zone 1 is 0 to 20° C., preferably 0 to 10° C., and more preferably 5 to 10° C.

The temperature in the temperature zone 2 is 30 to 90° C., preferably 40 to 80° C., more preferably 50 to 70° C., and still more preferably 60 to 70° C.

The temperature in the temperature zone 3 is 0 to 40° C., preferably 5 to 30° C., more preferably 5 to 20° C., and still more preferably 5 to 10° C.

The temperature in the temperature zone 4 is 0 to 40° C., preferably 5 to 30° C., more preferably 5 to 20° C., and even more preferably 5 to 10° C.

The yield of the bis(3,5,5-trimethylhexanoyl) peroxide is ≥91%; preferably, the yield of the bis(3,5,5-trimethylhexanoyl) peroxide is the rate is ≥92%.

The content of the bis(3,5,5-trimethylhexanoyl) peroxide is ≥91%; preferably, the content of the bis(3,5,5-trimethylhexanoyl) peroxide is ≥93%.

The target product bis(3,5,5-trimethylhexanoyl) peroxide has a chloride ion content of 0.02 wt. % to 0.05 wt. %, and a $H_2O_2$ content of 0.05 wt. % to 0.1 wt. %.

The hydrogen peroxide concentration is 30 wt. % to 50 wt. %.

The base is selected from water-soluble metal hydroxide, water-soluble quaternary ammonium hydroxide, water-soluble tertiary amine, water-soluble metal carbonate or water-soluble metal phosphate, preferably alkali metal hydroxide, water-soluble metal carbonic acid Salt or alkaline earth metal hydroxide, more preferably lithium hydroxide, sodium hydroxide, potassium hydroxide, sodium carbonate, potassium carbonate.

The mass concentration of lye is 5 wt. % to 45 wt. %, preferably 15 wt. % to 35 wt. %, and more preferably 20 wt. % to 30 wt. %.

The flow rate of lye is 1 to 4 L/h, preferably 1.5 to 3 L/h, and more preferably 1.8 to 2.5 L/h.

The hydrogen peroxide flow rate is 0.3 to 1 L/h, preferably 0.5 to 0.8 L/h, and more preferably 0.6 to 0.7 L/h.

The flow rate of the 3,5,5-trimethylhexanoyl chloride is 1 to 3 L/h, preferably 1.5 to 2.5 L/h, and more preferably 1.5 to 2 L/h.

The molar ratio of the hydrogen peroxide to 3,5,5-trimethylhexanoyl chloride is 0.5:1 to 0.8:1, preferably 0.55:1 to 0.75:1, and more preferably 0.6:1 to 0.7:1.

The molar ratio of the base to 3,5,5-trimethylhexanoyl chloride is 1:1 to 1.4:1, preferably 1.1:1 to 1.3:1, and more preferably 1.15:1 to 1.2:1.

In some embodiments, when the organic peroxide is bis(2-ethylhexyl) peroxydicarbonate, the oxidation substrate is -2 ethylhexyl chloroformate, and the catalyst is a base. Among them, preferably:

The temperature in the temperature zone 1 is 0 to 20° C., preferably 0 to 10° C., and more preferably 5 to 10° C.

The temperature in the temperature zone 2 is 10 to 40° C., preferably 15 to 35° C., and more preferably 20 to 30° C.

The temperature in the temperature zone 3 is 0 to 20° C., preferably 0 to 10° C., and more preferably 5 to 10° C.

The temperature in the temperature zone 4 is 0 to 20° C., preferably 0 to 10° C., and more preferably 5 to 10° C.

The yield of the bis(2-ethylhexyl) peroxydicarbonate is ≥86.5%; preferably, the yield of the bis(2-ethylhexyl) peroxydicarbonate is ≥90%.

The content of the bis(2-ethylhexyl) peroxydicarbonate is ≥95%; preferably, the content of the bis(2-ethylhexyl) peroxydicarbonate is ≥96%.

The target product has a chloride ion content of bis(2-ethylhexyl dicarbonate) of 0.02 to 0.05 wt. % and a content of $H_2O_2$ of 0.05 to 0.1 wt. %.

The mass concentration of hydrogen peroxide is 30% to 50%.

The base is selected from water-soluble metal hydroxide, water-soluble quaternary ammonium hydroxide, water-soluble tertiary amine, water-soluble metal carbonate or water-soluble metal phosphate, preferably alkali metal hydroxide, water-soluble metal carbonate Salt or alkaline earth metal hydroxide, more preferably sodium hydroxide, potassium hydroxide, sodium carbonate, potassium carbonate or lithium hydroxide.

The mass concentration of lye is 5% to 45%, preferably 15% to 35%, and more preferably 20% to 30%.

The flow rate of lye is 1 to 4 L/h, preferably 1.5 to 3 L/h, and more preferably 1.8 to 2.5 L/h.

The hydrogen peroxide flow rate is 0.3 to 1 L/h, preferably 0.5 to 0.8 L/h, and more preferably 0.6 to 0.7 L/h.

The flow rate of the 2-ethylhexyl chloroformate is 1 to 3 L/h, preferably 1.5 to 2.5 L/h, and more preferably 1.5 to 2 L/h.

The molar ratio of the hydrogen peroxide to 2-ethylhexyl chloroformate is 0.5:1 to 0.8:1, preferably 0.55:1 to 0.75:1, and more preferably 0.6:1 to 0.7:1.

The molar ratio of the base to 2-ethylhexyl chloroformate is 1:1 to 1.4:1, preferably 1.1:1 to 1.3:1, and more preferably 1.15:1 to 1.2:1.

It should be noted that the mass concentration of hydrogen peroxide, catalyst and oxidation substrate used in actual production (including laboratory, pilot test, and actual production process) will have a deviation of ±2 percentage points.

The second target of the present disclosure is to provide an online continuous flow production process, which is dedicated to any one of the aforementioned forms of processes, that is, a plug-and-produce type integrated continuous flow reactor. The integrated continuous flow reactor adopts a unitized structure, including the oxidation unit and a workup unit, where: the oxidation unit is used for the reaction to form alkyl peroxides and dialkyl peroxides, peroxycarboxylic acids, diacyl peroxides, peroxydicarbonates and peroxydiketals by using hydrogen peroxide, a catalyst, and an oxidized substrate; the workup unit is used to workup the products of organic peroxides.

The third target of the present disclosure is to provide an online continuous flow production process, which is dedicated to any one of the aforementioned forms of processes, that is, a plug-and-produce type integrated continuous flow reactor. The integrated continuous flow reactor adopts a unitized structure, each unit independently includes more than one reactor module or reactor module group, where, the reactor module group is composed of multiple reactor modules connected in series or in parallel, and each unit is connected in series with each other.

The fourth target of the present disclosure is to provide an online continuous flow production process, which is dedicated to any one of the aforementioned forms of processes, that is, a plug-and-produce type integrated continuous flow reactor. Adopting a unitized structure, each of the units corresponds to at least one temperature zone, and each temperature zone independently contains more than one reactor module or reactor module group, wherein the reactor module group is composed of multiple reactor modules in series or in parallel, and each temperature zone is connected in series with each other.

The above three continuous flow reactors can further be:

In some embodiments, the units further include a buffer vessel. The buffer is a container with a certain volume, which is mainly used to buffer pressure fluctuations and balance flow differences of the system, so that the system works more smoothly.

In some embodiments, the number of the inlets of the integrated continuous flow reactor is one or more, and the number of the outlets of the integrated continuous flow reactor is one or more.

In some embodiments, the reactor module is optionally any type of reactor capable of realizing a continuous flow process, and the reactor is any one or more selected from a microreactor, a Tandem loop reactor, and a tube. The microreactor, also known as a micro-structure reactor or a micro-channel reactor, is a device in which chemical reactions occur in a limited area with a generally lateral dimension of 1 mm and below. The micro-channel is the most typical form of such limited areas. The series coil reactor, that is, a reactor composed of a series of coil reactors connected in series by a pipe, in which the coil reactor is a tubular reactor in coil form. Tubular reactor is a kind of continuous operation reactor with tubular shape and large aspect ratio, which firstly appeared in the middle of the last century. This type of reactor can be very long; it can be a single tube or multiple tubes in parallel; it also can be empty or filled.

In some embodiments, the reactor may be one or more.

In some embodiments, the materials of the reactor channel include the single crystal silicon, special glass, ceramic, stainless steel or metal alloy with a corrosion-resistant coating, and polytetrafluoroethylene.

In some embodiments, the reactor modules, the reactor module groups, the reactor modules and the reactor module groups are all connected in series or in parallel, respectively.

In some embodiments, the continuous flow production process is performed in a plug-and-produce integrated continuous flow reactor including 4 temperature zones.

In some embodiments, the plug-and-produce integrated continuous flow reactor includes at least 4 temperature zones.

In some embodiments, the oxidation unit corresponds to temperature zone 1 to temperature zone 3, and the workup unit corresponds to temperature zone 4.

In some embodiments, the temperature in the temperature zone 1 is 0 to 60° C., preferably 0 to 40° C., more preferably 5 to 30° C., more preferably 5 to 20° C., and even more preferably 5 to 10° C.

In some embodiments, the temperature in the temperature zone 2 is 30 to 110° C., preferably 40 to 100° C., more preferably 50 to 90° C., more preferably 60 to 80° C., and more preferably 65 to 70° C.

In some embodiments, the temperature in the temperature zone 3 is 0 to 50° C., preferably 0 to 40° C., more preferably 5 to 30° C., more preferably 5 to 20° C., and even more preferably 5 to 10° C.

In some embodiments, the temperature in the temperature zone 4 is 0 to 50° C., preferably 0 to 40° C., more preferably 5 to 30° C., more preferably 5 to 20° C., and even more preferably 5 to 10° C.

The fifth target of the present disclosure is to provide a chemical production process, which includes the online continuous flow production process for preparing organic peroxides directly from alcohols or alkanes, and one or more follow-up production process. For example, the chemical production process may be a polymerization process. The organic peroxide produced by the online continuous flow production process of the present disclosure is used as an initiator of the polymerization process, and the process and the polymerization reaction process can be seamlessly docked. This combination can form a complete continuous "produce-to-use" of organic peroxides, overturning the existing produce-storage-transport-storage-use mode, and realize a new production mode which is so-called "produce-to-use".

The six target of the present disclosure is to provide a chemical production equipment, the mentioned chemical production equipment includes the any form of the plug-and-produce integrated continuous flow reactor for online continuous flow production process in this disclosure, and one or more subsequent production equipment. For example, the chemical production equipment can be a polymer production equipment, and the plug-and-produce integrated continuous flow reactor of the present disclosure can be directly connected to a polymerization kettle seamlessly. It can form a complete continuous production equipment to produce-and-use organic peroxides, overturning the existing produce-storage-transport-storage-use mode and realize a new production mode which is so-called "produce-to-use".

The present disclosure has the following beneficial effects:

1. The disclosure realizes the efficient continuous flow synthesis of organic peroxides on a plug-and-produce integrated continuous flow reactor. That is, the reactants are continuously fed into the reactor and the product is continuously collected. With the help of functional unit temperature zone division and optimization of temperature settings, the efficiency of the process is greatly improved. The production time is equal to or less than 6 minutes.

2. The process safety is greatly improved, the relatively small liquid holding capacity and excellent heat transfer characteristics of the continuous flow reactor, and the shorter reaction time (within 6 minutes) make the process safer. The liquid holding capacity of the reactor refers to the total volume of the reaction material stored in the reactor at any time, when the operation reaches a steady state.

3. According to the different self-accelerated decomposition temperature and thermal stability of organic peroxides and the physical and chemical properties of the raw materials, two functional units are designed in the plug-and-produce integrated continuous flow reactor, including the oxidation unit and the workup. Wherein, the oxidation unit and a workup unit, where: the oxidation unit is used for the reaction to form alkyl peroxides and dialkyl peroxides, peroxycarboxylic acids, diacyl peroxides, peroxydicarbonates and peroxydiketalsby using hydrogen peroxide, a catalyst, and an oxidized substrate; the workup unit is used to workup the products of organic peroxides. The synergistic effect of the two functional units overcome the defects of the existing technologies, achieving a high efficiency, high quality, and large-scale production of organic peroxides.

4. In the plug-and-produce integrated continuous flow reactor, the product quality is stable and reproducible due to the stable flow rate and stable production process.

5. This process can also complete the reaction in equal to or less than 6 minutes on the industrial scale, and the product content and yield are basically the same as in the laboratory scale without scaling-up effect, which solved the problem of industrial scale-up of the organic peroxide continuous flow process.

6. The plug-and-produce integrated continuous flow reactor has a small volume and a small footprint, which greatly saves plant land.

Chinese patent CN101287704 disclosed a method for producing organic peroxides through micro-reaction technology, its main differences from the present disclosure are as follows:

First, since the static mixer mentioned in CN101287704 does not have heat exchanger, an external heat exchanger is required to exchange the heat. Thus, there no heat exchange when the materials in contact, the static mixer does not actually solve the heat exchange problem, so the reaction temperature is low, and all synthesis temperature is below 25° C.

Second, the lower reaction temperature leads to a long production time: The reaction time is about 2.5-17 mins, and the workup time is 1-2 hours, so the total production time is greater than 1 hour. The production time refers to the time required for the output of commercially available products, which is also referred to as residence time in a continuous flow process.

Third, in CN101287704, the method is preferred to use the assistance of high frequency vibration directly or indirectly, however, the use of high frequency vibration such as ultrasound has an inevitable scaling-up effect.

Fourth, the method in CN101287704 can synthesize the organic peroxides, include dialkyl peroxides, peroxycarboxylic acids, diacyl peroxides, peroxydicarbonates, and peroxydiketals, but alkyl peroxides cannot be synthesized by this process, indicating the limitations of the method in this patent.

DETAILED DESCRIPTION OF THE DISCLOSURE

The present disclosure will be further described with reference to specific cases. It should be claimed that these examples are only used to illustrate present disclosure and not to limit the its scope. In addition, it should be understood that when people make any changes or modifications according to the present disclosure after reading the present disclosure, these equivalent forms also fall within the scope defined by the appended claims of the present disclosure.

The concentration in the examples of the present disclosure is the mass concentration. The product content is measured by effective oxygen titration (iodometric method). The chloride ion content is detected by an ion-detector. Other organic peroxides are analyzed by high performance liquid chromatography (HPLC) or effective oxygen titration (iodometric method). Content of alkyl peroxide products and other organic peroxides ($H_2O_2$ and dialkyl peroxide) in the present disclosure is 0.05 to 0.1 wt. %. The $H_2O_2$ content of products, such as alkyl peroxide, carbon peroxide and diketone peroxide, is 0.05 to 0.1 wt. %. For xylene peroxide and peroxydicarbonate products, chloride ion content is 0.02 wt. % to 0.05 wt. %, and $H_2O_2$ content is 0.05 wt. % to 0.1 wt. %. No delay line is required in the reactor.

It should be noted that the mass concentration of hydrogen peroxide, catalyst and oxidized substrate used in actual production (including laboratory, pilot test, and actual production process) will have deviations of ±2%. The temperature will have a deviation of ±3° C. And production time will have a deviation of ±5 s.

USED ABBREVIATIONS

Figure 1:
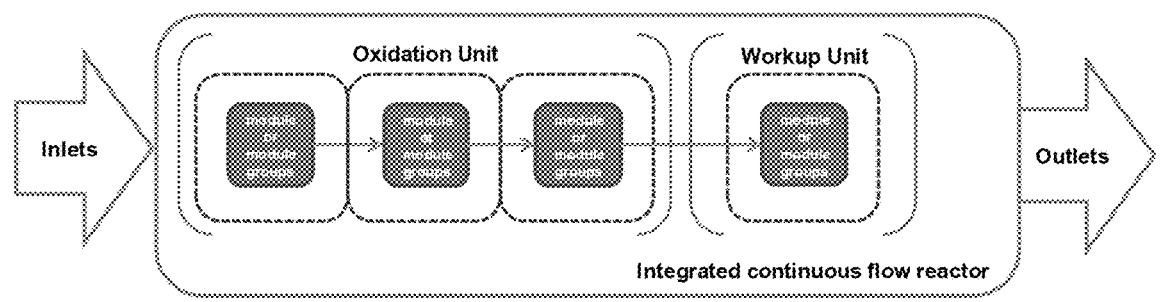
FIG. 1 is a diagram of a continuous flow production process according to the disclosure.
Figure 2:
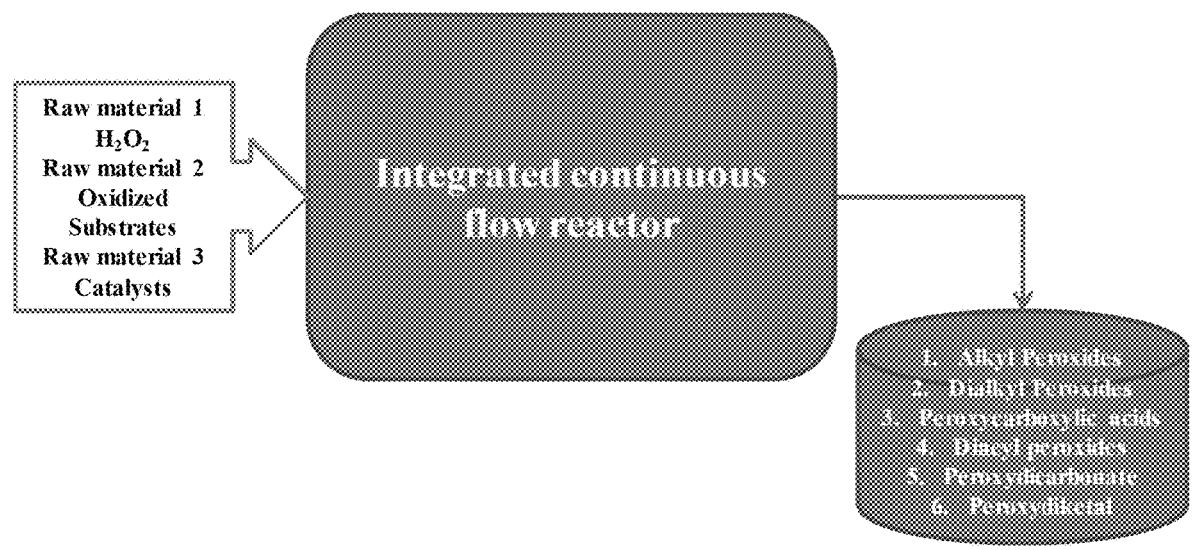
FIG. 2 is a schematic diagram of an integrated reactor according to the disclosure.

TBA: tert-Butanol
TAA: tert-amyl alcohol
2-EHCF: 2-ethylhexyl chloroformate
NSC904: 2,4,4-trimethyl-2-pentanol
IBCL: isobutyrylchloride
TMHC: 3,5,5-trimethylhexanoyl chloride
MEK: methyl ethyl ketone
IPCF: isopropyl chloroformate
ACAC: acetylacetone
3-MOCF: 3-methoxybutyl chloroformate
2-EOCF: 2-ethoxyethyl chloroformate
BCF: butyl chlorocarbonate
MIBK: methyl isobutyl ketone EXAMPLES 1-8 PREPARATION OF bis(3,5,5-trimethylhexanoyl) peroxide As shown in FIGS. 1 and 2, raw material 1 (aqueous hydrogen peroxide solution), raw material 2 (alkali solution), and raw material 3 (oxidized substrate) are successively fed into a continuous reactor by a constant flow pump. They sequentially flow from temperature zone 1 to temperature zone 3 during which the reaction is complete. Then reaction liquid flows out of the temperature zone 3 and enters the temperature zone 4 for workup, after which the final product would be obtained. Feed rate 1 represents the feed rate of raw material 1, Feed rate 2 represents the feed rate of raw material 2, and feed rate 3 represents the feed rate of raw material 3.

| Examples | | Example 1 | Example 2 | Example 3 | Example 4 |
|---|---|---|---|---|---|
| Feed rate 1 | Property | $H_2O_2/H_2O$ | $H_2O_2/H_2O$ | $H_2O_2/H_2O$ | $H_2O_2/H_2O$ |
| | Weight % | 30 | 30 | 30 | 30 |
| | L/h | 0.55 | 2.04 | 10.7 | 0.92 |
| Feed rate 2 | Property | $KOH/H_2O$ | $KOH/H_2O$ | $KOH/H_2O$ | $KOH/H_2O$ |
| | Weight % | 35 | 20 | 20 | 45 |
| | L/h | 1.36 | 7.18 | 3.66 | 1.65 |
| Feed rate 3 | Property | TMHC | TMHC | TMHC | TMHC |
| | Weight % | 98 | 98 | 98 | 98 |
| | L/h | 2.02 | 6.75 | 3.29 | 2.42 |
| Total feed rate | L/h | 4.04 | 15.97 | 8.02 | 5.05 |
| Temperature zone 1 | °C. | 0 | 5 | 5 | 5 |
| Temperature zone 2 | °C. | 30 | 40 | 50 | 60 |
| Temperature zone 3 | °C. | 0 | 5 | 10 | 20 |
| Temperature zone 4 | °C. | 0 | 5 | 10 | 20 |
| $KOH:H_2O_2:TMHC$ | | 1:0.5:1 | 1.15:0.55:1 | 1.2:0.6:1 | 1.3:0.7:1 |
| Production time | min | 3.6 | 1.0 | 2.0 | 2.66 |
| Yield | % | 91.8 | 92.3 | 92.0 | 92.1 |
| Content | % | 93 | 92.2 | 91.6 | 91.0 |

| Examples | | Example 5 | Example 6 | Example 7 | Example 8 |
|---|---|---|---|---|---|
| Feed rate 1 | Property | $H_2O_2/H_2O$ | $H_2O_2/H_2O$ | $H_2O_2/H_2O$ | $H_2O_2/H_2O$ |
| | Weight % | 30 | 50 | 30 | 30 |
| | L/h | 0.83 | 0.53 | 0.48 | 24.9 |
| Feed rate 2 | Property | $KOH/H_2O$ | $KOH/H_2O$ | $KOH/H_2O$ | $KOH/H_2O$ |
| | Weight % | 15 | 5 | 20 | 15 |
| | L/h | 4.43 | 10.4 | 1.77 | 132.9 |
| Feed rate 3 | Property | TMHC | TMHC | TMHC | TMHC |
| | Weight % | 98 | 98 | 98 | 98 |
| | L/h | 2.02 | 2.02 | 1.74 | 60.6 |
| Total feed rate | L/h | 7.28 | 12.95 | 3.99 | 218.4 |
| Temperature zone 1 | °C. | 0 | 10 | 20 | 0 |
| Temperature zone 2 | °C. | 70 | 80 | 90 | 70 |
| Temperature zone 3 | °C. | 30 | 40 | 10 | 30 |
| Temperature zone 4 | °C. | 30 | 40 | 10 | 30 |
| $KOH:H2O_2:TMHC$ | | 1.4:0.75:1 | 1.1:0.8:1 | 1.1:0.5:1 | 1.4:0.75:1 |
| Production time | min | 2.2 | 1.23 | 4.0 | 2.2 |
| Yield | % | 91.8 | 92.1 | 92.0 | 91.7 |
| Content | % | 91.5 | 91.2 | 91.0 | 91.6 |

EXAMPLES 9-18 PREPARATION OF tert-butyl hydroperoxide

As shown in FIGS. 1 and 2, raw material 1 (acidic solution), raw material 2 (oxidized substrate), and raw material 3 (aqueous hydrogen peroxide solution) are successively fed into a continuous reactor by a constant flow pump. They sequentially flow from temperature zone 1 to temperature zone 3 during which the reaction is complete. Then reaction liquid flows out of the temperature zone 3 and enters the temperature zone 4 for workup, after which the final product would be obtained. Feed rate 1 represents the feed rate of raw material 1, Feed rate 2 represents the feed rate of raw material 2, and feed rate 3 represents the feed rate of raw material 3.

| Examples | | | Example 9 | Example 10 | Example 11 | Example 12 | Example 13 |
|---|---|---|---|---|---|---|---|
| Feed rate 1 | Property | | $H_2SO_4/H_2O$ | $H_2SO_4/H_2O$ | $H_2SO_4/H_2O$ | $H_2SO_4/H_2O$ | $H_2SO_4/H_2O$ |
| | Weight % | | 50 | 70 | 70 | 80 | 70 |
| | | L/h | 1.79 | 2.06 | 1.14 | 1.17 | 2.11 |
| Feed rate 2 | Property | | $TBA/H_2O$ | $TBA/H_2O$ | $TBA/H_2O$ | $TBA/H_2O$ | $TBA/H_2O$ |
| | Weight % | | 94.3 | 94.3 | 94.3 | 94.3 | 94.3 |
| | | L/h | 2.6 | 2.6 | 2.17 | 2.17 | 4.29 |
| Feed rate 3 | Property | | $H_2O_2/H_2O$ | $H_2O_2/H_2O$ | $H_2O_2/H_2O$ | $H_2O_2/H_2O$ | $H_2O_2/H_2O$ |
| | Weight % | | 50 | 50 | 50 | 30 | 50 |
| | | L/h | 1.54 | 1.17 | 1.1 | 2.03 | 2.66 |
| Total feed rate | | L/h | 5.93 | 5.83 | 4.41 | 5.37 | 9.06 |
| Temperature zone 1 | | °C. | 5 | 20 | 30 | 40 | 0 |
| Temperature zone 2 | | °C. | 85 | 40 | 50 | 60 | 85 |
| Temperature zone 3 | | °C. | 5 | 30 | 40 | 10 | 0 |
| Temperature zone 4 | | °C. | 5 | 30 | 40 | 10 | 0 |
| $H_2SO_4:H_2O_2:TBA$ | | | 0.5:1.05:1 | 1:0.8:1 | 0.6:0.9:1 | 0.7:1:1 | 0.6:1.1:1 |
| Production time | | min | 2.9 | 3.0 | 4.0 | 3.3 | 2.0 |
| Yield | | % | 75.4 | 72.4 | 72.6 | 71.3 | 75.4 |
| Content | | % | 83 | 80.6 | 80.5 | 81.1 | 80 |
| Examples | | | Example 14 | Example 15 | Example 16 | Example 17 | Example 18 |
| Feed rate 1 | Property | | $H_2SO_4/H_2O$ | $H_2SO_4/H_2O$ | $H_2SO_4/H_2O$ | $H_2SO_4/H_2O$ | $H_2SO_4/H_2O$ |
| | Weight % | | 60 | 70 | 70 | 90 | 50 |
| | | L/h | 1.49 | 2.06 | 4.22 | 1.04 | 53.7 |
| Feed rate 2 | Property | | $TBA/H_2O$ | $TBA/H_2O$ | $TBA/H_2O$ | $TBA/H_2O$ | $TBA/H_2O$ |
| | Weight % | | 94.3 | 94.3 | 94.3 | 94.3 | 94.3 |
| | | L/h | 2.6 | 2.6 | 8.58 | 2.17 | 78 |
| Feed rate 3 | Property | | $H_2O_2/H_2O$ | $H_2O_2/H_2O$ | $H_2O_2/H_2O$ | $H_2O_2/H_2O$ | $H_2O_2/H_2O$ |
| | Weight % | | 50 | 50 | 50 | 50 | 50 |
| | | L/h | 1.76 | 1.54 | 5.32 | 1.28 | 46.2 |
| Total feed rate | | L/h | 5.84 | 6.2 | 18.12 | 4.49 | 177.9 |
| Temperature zone 1 | | °C. | 0 | 10 | 5 | 5 | 5 |
| Temperature zone 2 | | °C. | 70 | 90 | 100 | 80 | 85 |
| Temperature zone 3 | | °C. | 20 | 30 | 10 | 5 | 5 |
| Temperature zone 4 | | °C. | 20 | 30 | 10 | 5 | 5 |
| $H_2SO_4:H_2O_2:TBA$ | | | 0.5:1.2:1 | 0.9:1.05:1 | 0.6:1.05:1 | 0.7:1.05:1 | 0.5:1.05:1 |
| Production time | | min | 3.2 | 2.89 | 1.0 | 3.73 | 2.9 |
| Yield | | % | 75.4 | 72.4 | 72.6 | 71.3 | 75.8 |
| Content | | % | 84 | 80.6 | 82.5 | 81.1 | 83.2 |

EXAMPLES 19-28 PREPARATION OF tert-amyl hydrogen peroxide

Operating as Examples 9-18

| Examples | | | Example 19 | Example 20 | Example 21 | Example 22 | Example 23 |
|---|---|---|---|---|---|---|---|
| Feed rate 1 | Property | | $H_2SO_4/H_2O$ | $H_2SO_4/H_2O$ | $H_2SO_4/H_2O$ | $H_2SO_4/H_2O$ | $H_2SO_4/H_2O$ |
| | Weight % | | 70 | 60 | 70 | 80 | 50 |
| | | L/h | 1.76 | 1.87 | 1.41 | 1.4 | 2.7 |
| Feed rate 2 | Property | | $TAA/H_2O$ | $TAA/H_2O$ | $TAA/H_2O$ | $TAA/H_2O$ | $TAA/H_2O$ |
| | Weight % | | 98 | 98 | 98 | 98 | 98 |
| | | L/h | 2.22 | 2.02 | 1.78 | 2.02 | 2.22 |

|  |  | -continued |  |  |  |  |
|---|---|---|---|---|---|---|
| Feed rate 3 | Property | H$_2$O$_2$/H$_2$O | H$_2$O$_2$/H$_2$O | H$_2$O$_2$/H$_2$O | H$_2$O$_2$/H$_2$O | H$_2$O$_2$/H$_2$O |
|  | Weight % | 50 | 30 | 50 | 50 | 50 |
|  | L/h | 1.28 | 1.53 | 0.9 | 1.16 | 1.35 |
| Total feed rate | L/h | 5.26 | 5.42 | 4.08 | 4.58 | 6.29 |
| Temperature zone 1 | °C. | 5 | 10 | 20 | 30 | 40 |
| Temperature zone 2 | °C. | 85 | 90 | 100 | 70 | 80 |
| Temperature zone 3 | °C. | 30 | 5 | 10 | 20 | 30 |
| Temperature zone 4 | °C. | 30 | 5 | 10 | 20 | 30 |
| H$_2$SO$_4$:H$_2$O$_2$:TAA |  | 1:1.14:1 | 1:0.9:1 | 1:1:1 | 1:1.14:1 | 1.1:1.2:1 |
| Production time | min | 3.1 | 3.0 | 4.0 | 3.4 | 2.6 |
| Yield | % | 79.3 | 77.4 | 74.6 | 73.3 | 79.3 |
| Content | % | 84.2 | 84.0 | 83.9 | 84.4 | 84.2 |

| Examples |  | Example 24 | Example 25 | Example 26 | Example 27 | Example 28 |
|---|---|---|---|---|---|---|
| Feed rate 1 | Property | H$_2$SO$_4$/H$_2$O | H$_2$SO$_4$/H$_2$O | H$_2$SO$_4$/H$_2$O | H$_2$SO$_4$/H$_2$O | H$_2$SO$_4$/H$_2$O |
|  | Weight % | 70 | 70 | 90 | 70 | 70 |
|  | L/h | 1.76 | 4.52 | 1.23 | 2.63 | 52.8 |
| Feed rate 2 | Property | TAA/H$_2$O | TAA/H$_2$O | TAA/H$_2$O | TAA/H$_2$O | TAA/H$_2$O |
|  | Weight % | 98 | 98 | 98 | 98 | 98 |
|  | L/h | 2.22 | 7.13 | 2.22 | 3.5 | 66.6 |
| Feed rate 3 | Property | H$_2$O$_2$/H$_2$O | H$_2$O$_2$/H$_2$O | H$_2$O$_2$/H$_2$O | H$_2$O$_2$/H$_2$O | H$_2$O$_2$/H$_2$O |
|  | Weight % | 50 | 50 | 50 | 50 | 50 |
|  | L/h | 1.7 | 4.66 | 1.28 | 2 | 38.4 |
| Total feed rate | L/h | 5.38 | 16.31 | 4.73 | 8.13 | 157.8 |
| Temperature zone 1 | °C. | 0 | 10 | 10 | 5 | 5 |
| Temperature zone 2 | °C. | 85 | 40 | 50 | 60 | 85 |
| Temperature zone 3 | °C. | 40 | 0 | 10 | 30 | 30 |
| Temperature zone 4 | °C. | 40 | 0 | 10 | 30 | 30 |
| H$_2$SO$_4$:H$_2$O$_2$:TAA |  | 1:1.25:1 | 0.8:1.3:1 | 0.9:1.14:1 | 0.95:1.14:1 | 1:1.14:1 |
| Production time | min | 3.0 | 1.0 | 3.5 | 2.0 | 3.0 |
| Yield | % | 79.3 | 77.4 | 74.6 | 73.3 | 79.6 |
| Content | % | 84.2 | 84.0 | 83.9 | 84.4 | 84.6 |

EXAMPLES 29-36 PREPARATION OF bis(2-ethylhexyl) peroxydicarbonate

Operating as Examples 1-8

| Examples |  | Example 29 | Example 30 | Example 31 | Example 32 |
|---|---|---|---|---|---|
| Feed rate 1 | Property | H$_2$O$_2$/H$_2$O | H$_2$O$_2$/H$_2$O | H$_2$O$_2$/H$_2$O | H$_2$O$_2$/H$_2$O |
|  | Weight % | 30 | 30 | 30 | 50 |
|  | L/h | 0.55 | 2.54 | 0.88 | 0.48 |
| Feed rate 2 | Property | Na$_2$CO$_3$/H$_2$O | K$_2$CO$_3$/H$_2$O | LiOH/H$_2$O | KOH/H$_2$O |
|  | Weight % | 20 | 20 | 15 | 5 |
|  | L/h | 2.33 | 9.8 | 2.9 | 9.8 |
| Feed rate 3 | Property | 2-EHCF | 2-EHCF | 2-EHCF | 2-EHCF |
|  | Weight % | 98 | 98 | 98 | 98 |
|  | L/h | 2.03 | 7.82 | 2.3 | 1.83 |
| Total feed rate | L/h | 4.8 | 20.2 | 6.09 | 4.23 |
| Temperature zone 1 | °C. | 0 | 5 | 10 | 20 |
| Temperature zone 2 | °C. | 10 | 15 | 20 | 30 |
| Temperature zone 3 | °C. | 0 | 5 | 10 | 20 |
| Temperature zone 4 | °C. | 0 | 5 | 10 | 20 |

-continued

| Alkali:H$_2$O$_2$:2-EHCF | | 1.2:0.5:1 | 1.2:0.6:1 | 1.4:0.7:1 | 1.15:0.8:1 |
|---|---|---|---|---|---|
| Production time | min | 3.71 | 1.0 | 3.0 | 4.0 |
| Yield | % | 90.4 | 88.6 | 87.8 | 86.5 |
| Content | % | 96.2 | 95.8 | 96.0 | 95.6 |

| Examples | | Example 33 | Example 34 | Example 35 | Example 36 |
|---|---|---|---|---|---|
| Feed rate 1 | Property | H$_2$O$_2$/H$_2$O | H$_2$O$_2$/H$_2$O | H$_2$O$_2$/H$_2$O | H$_2$O$_2$/H$_2$O |
| | Weight % | 30 | 30 | 30 | 30 |
| | L/h | 0.55 | 1.09 | 0.75 | 22.5 |
| Feed rate 2 | Property | KOH/H$_2$O | KOH/H$_2$O | KOH/H$_2$O | KOH/H$_2$O |
| | Weight % | 25.5 | 25.5 | 45 | 45 |
| | L/h | 2.4 | 3.95 | 1.04 | 31.2 |
| Feed rate 3 | Property | 2-EHCF | 2-EHCF | 2-EHCF | 2-EHCF |
| | Weight % | 98 | 98 | 98 | 98 |
| | L/h | 2.03 | 3.6 | 1.83 | 54.9 |
| Total feed rate | L/h | 4.98 | 8.7 | 3.61 | 108.3 |
| Temperature zone 1 | °C. | 5 | 10 | 5 | 5 |
| Temperature zone 2 | °C. | 35 | 40 | 30 | 30 |
| Temperature zone 3 | °C. | 5 | 5 | 5 | 5 |
| Temperature zone 4 | °C. | 5 | 5 | 5 | 5 |
| KOH:H$_2$O$_2$:2-EHCF | | 1.3:0.5:1 | 1.2:0.55:1 | 1.1:0.75:1 | 1.1:0.75:1 |
| Production time | min | 3.47 | 2.0 | 4.72 | 4.72 |
| Yield | % | 90.1 | 88.9 | 87.9 | 87.4 |
| Content | % | 95.2 | 95.6 | 96.6 | 96.2 |

EXAMPLES 37-38 PREPARATION OF 1,1,3,3-tetramethyl butyl hydroperoxide

Operating as Examples 9-18

| Examples | | Example 37 | Example 38 |
|---|---|---|---|
| Feed rate 1 | Property | H$_2$SO$_4$/H$_2$O | H$_2$SO$_4$/H$_2$O |
| | Weight % | 80 | 90 |
| | L/h | 0.79 | 0.7 |
| Feed rate 2 | Property | NSC904 | NSC904 |
| | Weight % | 95 | 95 |
| | L/h | 3.15 | 3.15 |
| Feed rate 3 | Property | H$_2$O$_2$/H$_2$O | H$_2$O$_2$/H$_2$O |
| | Weight % | 50 | 50 |
| | L/h | 1.08 | 1.08 |
| Total feed rate | L/h | 5.02 | 4.93 |
| Temperature zone 1 | °C. | 5 | 5 |
| Temperature zone 2 | °C. | 110 | 70 |
| Temperature zone 3 | °C. | 30 | 30 |
| Temperature zone 4 | °C. | 30 | 30 |
| H$_2$SO$_4$:H$_2$O$_2$:NSC904 | | 0.56:1.04:1 | 0.56:1.04:1 |
| Production time | min | 3.2 | 3.26 |
| Yield | % | 76.4 | 73.4 |
| Content | % | 79.3 | 79.6 |

EXAMPLES 39-43

Operating as Examples 9-18

| Examples | | Example 39 | Example 40 | Example 41 | Example 42 | Example 43 |
|---|---|---|---|---|---|---|
| Feed rate 1 | Property | CF$_3$COOH/H$_2$O | H$_2$SO$_4$/H$_2$O | H$_2$SO$_4$/H$_2$O | H$_3$PO$_4$/H$_2$O | H$_2$SO$_4$/H$_2$O |
| | Weight % | 70 | 50 | 60 | 70 | 70 |
| | L/h | 2.46 | 2.46 | 2.05 | 1.7 | 1.65 |
| Feed rate 2 | Property | TBA/H$_2$O | TAA/H$_2$O | MEK | MIBK | ACAC |
| | Weight % | 94.3 | 98 | 98 | 98 | 98 |
| | L/h | 2.6 | 2.22 | 1.83 | 2.43 | 1.97 |
| Feed rate 3 | Property | H$_2$O$_2$/H$_2$O | H$_2$O$_2$/H$_2$O | H$_2$O$_2$/H$_2$O | H$_2$O$_2$/H$_2$O | H$_2$O$_2$/H$_2$O |
| | Weight % | 50 | 50 | 50 | 50 | 50 |
| | L/h | 0.74 | 0.56 | 2.04 | 2.43 | 1.92 |
| Total feed rate | L/h | 5.8 | 5.24 | 5.92 | 6.56 | 5.54 |
| Temperature zone 1 | °C. | 5 | 5 | 5 | 5 | 5 |

-continued

| Examples | | Example 39 | Example 40 | Example 41 | Example 42 | Example 43 |
|---|---|---|---|---|---|---|
| Temperature zone 2 | °C. | 90 | 90 | 85 | 80 | 85 |
| Temperature zone 3 | °C. | 30 | 20 | 10 | 40 | 50 |
| Temperature zone 4 | °C. | 30 | 20 | 10 | 40 | 50 |
| Acid:$H_2O_2$:TBA/TAA/ MEK/MIBK/ACAC | | 1:1:0.5 | 1:1:0.6 | 1:1:2 | 1:1:2.5 | 1:1:2 |
| Production time | min | 3.5 | 3.76 | 3.33 | 3 | 3.56 |
| Yield | % | 94.3 | 93.6 | 73.2 | 74.7 | 75.5 |
| Content | % | 93.4 | 95.4 | 80.5 | 82.3 | 83.1 |

EXAMPLES 44-48

Operating as Examples 1-8

| Examples | | | Example 44 | Example 45 | Example 46 | Example 47 | Example 48 |
|---|---|---|---|---|---|---|---|
| Feed rate 1 | Property | | $H_2O_2/H_2O$ | $H_2O_2/H_2O$ | $H_2O_2/H_2O$ | $H_2O_2/H_2O$ | $H_2O_2/H_2O$ |
| | Weight % | | 30 | 30 | 30 | 30 | 30 |
| | L/h | | 0.55 | 0.55 | 0.55 | 0.55 | 0.66 |
| Feed rate 2 | Property | | KOH/$H_2O$ | KOH/$H_2O$ | KOH/$H_2O$ | KOH/$H_2O$ | KOH/$H_2O$ |
| | Weight % | | 15 | 20 | 30 | 35 | 45 |
| | L/h | | 3.47 | 2.83 | 2.04 | 1.89 | 1.51 |
| Feed rate 3 | Property | | IBCL | 3-MOCF | 2-EOCF | IPCF | BCF |
| | Weight % | | 98 | 98 | 98 | 98 | 98 |
| | L/h | | 1.08 | 1.54 | 1.37 | 1.42 | 1.57 |
| Total feed rate | L/h | | 5.1 | 4.92 | 3.96 | 3.86 | 3.74 |
| Temperature zone 1 | °C. | | 5 | 5 | 5 | 5 | 5 |
| Temperature zone 2 | °C. | | 30 | 30 | 40 | 50 | 30 |
| Temperature zone 3 | °C. | | 5 | 5 | 5 | 5 | 0 |
| Temperature zone 4 | °C. | | 5 | 5 | 5 | 5 | 0 |
| KOH:$H_2O_2$:IBCL/3-MOCF/ 2EOCF/IPCF/BCF | | | 1.1:0.5:1 | 1.2:0.5:1 | 1.3:0.5:1 | 1.4:0.5:1 | 1.2:0.5:1 |
| Production time | min | | 3.5 | 3.63 | 4.5 | 4.6 | 4.7 |
| Yield | % | | 94.3 | 93.6 | 73.2 | 74.7 | 75.5 |
| Content | % | | 91.3 | 90.2 | 80.5 | 81.5 | 83.2 |

EXAMPLE 49

Operating as Examples 9-18

| Examples | | Example 49 |
|---|---|---|
| Feed rate 1 | Property | $H_2SO_4$ |
| | Weight % | 90 |
| | L/h | 0.03 |
| Feed rate 2 | Property | $AC_2O$ |
| | Weight % | 98 |
| | L/h | 1.73 |
| Feed rate 3 | Property | $H_2O_2/H_2O$ |
| | Weight % | 50 |
| | L/h | 0.74 |
| Total feed rate | L/h | 2.5 |
| Temperature zone 1 | °C. | 30 |
| Temperature zone 2 | °C. | 50 |
| Temperature zone 2 | °C. | 70 |
| Temperature zone 3 | °C. | 5 |
| Temperature zone 4 | °C. | 5 |
| $H_2SO_4$:$H_2O_2$:$AC_2O$ | | 1:2:1 |
| Production time | min | 3.2 |
| Yield | % | 76.7 |
| Content | % | 80 |

It can be seen from the above examples that the continuous flow synthesis of organic peroxides according to the present disclosure has a huge advantage in time, which has been shortened from several hours in the existing process to ≤6 minutes, and the overall yield and content are significantly improved. At the same time, it can be seen from Examples 5 and 8, 9 and 18, 19 and 28, 35 and 36 that the yield did not change after scale-up and the reaction time did not increase, indicating that the present disclosure does not have a magnifying effect.

Comparative Example 1 Preparation of Bis(3,5,5-trimethylhexanoyl) peroxide

|  | Comparative Example 1 | Chinese patent CN101287704A | Present disclosure |
|---|---|---|---|
| Process |  | Mix first, complete reaction within a certain retention volume after heat exchange to a proper temperature | Mix, reaction, and heat exchange are performed simultaneously, the reaction is maintained for a certain residence time |
| Temperature/° C. |  | 10-25 | 30-90 |
| Reaction Time(not include workup time)/min |  | 3.5-10 | 0.63 |
| yield % |  | 92 | 91.8-92.5 |
| Content % |  | 91 | 91-93 |

As can be seen from the above comparative Example 1, the process of the present disclosure is essentially different from the Chinese patent CN101287704A. The reaction can be completed at a higher temperature and in a shorter time. The yield and content remain unchanged and the reaction time is shortened by more than 82%.

What is claimed is:

1. An online continuous flow production method for the direct synthesis of organic peroxide, comprising
feeding raw material including hydrogen peroxide, a catalyst and an oxidized substrate continuously into inlets of a plug-and-produce integrated continuous flow reactor; wherein the plug-and-produce integrated continuous flow reactor comprises an oxidation unit and a workup unit; and
obtaining organic peroxide at outlets of the plug-and-produce integrated continuous flow reactor;
wherein the catalyst is acid or alkali, and the organic peroxide is selected from the group consisting of alkyl peroxide oxide, dialkyl peroxide, peroxycarboxylic acid, diacyl peroxide, peroxydicarbonate, and peroxyketal;
wherein the oxidized substrate is selected from the group consisting of alcohol, carboxylic acid, anhydride, ketone, acyl chloride, and chloroformate;
wherein a general formula of a production process inside the plug-and-produce integrated continuous flow reactor is as follows:

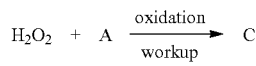

wherein A is the oxidation substrate, including alcohol, carboxylic acid, anhydride, ketone, acyl chloride and chloroformate; and C is alkyl peroxide, dialkyl peroxide, peroxycarboxylic acid, diacyl peroxide, peroxydicarbonate and peroxyketal.

2. The online continuous flow production method according to claim 1, wherein when A is acid chloride, the general formula is $R^1COCl$;

when A is chloroformate, the general formula is $R^2OCOCl$;
when A is alcohol, the general formula is $R^3(OH)n$, wherein n is an integer greater than 0;
when A is ketone, the general formula is $R^4R^{4'}(CO)$ or $R^4(CO)$ (Cyclone);
when A is carboxylic acid, the general formula is $R^5COOH$;
when A is carboxylic anhydride, the general formula is $(R^5CO)_2O$ or $R^5(CO)_2O$ (cyclic anhydride);
when C is a diacyl peroxide, the general formula is $R^1(COO)_2$;
when C is a peroxydicarbonate, the general formula is $R^2(OCOO)_2$;
when C is an alkyl peroxide, the general formula is $R^3(OOH)_n$, wherein n is an integer greater than 0;
when C is a dialkyl peroxide, the general formula is $R^3OOR^3$, where n=1;
when C is a diketal peroxide, the general formula is $R^4(OOOH)_2$;
when C is a peroxycarboxylic acid, the general formula is $R^5OOOH$;
$R^1$ is selected from $C_1$-$C_{20}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl;
$R^2$ is selected from $C_1$-$C_{20}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl;
$R^3$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl;
$R^4$ or $R^{4'}$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl;
$R^5$ is selected from $C_1$-$C_{12}$ saturated or unsaturated alkyl, unsubstituted or substituted aryl, unsubstituted or substituted heterocyclic aryl, unsubstituted or substituted saturated heterocycloalkyl, unsubstituted or substituted partially saturated heterocycloalkyl, unsubstituted or substituted cycloalkyl.

3. The online continuous flow production method according to claim 1, where in the organic peroxide is selected from the group consisting of diisobutyrylperoxide CAS NO: 3437-84-1, bis(3-methoxybutyl) peroxydicarbonate CAS NO: 52238-68-3, bis(ethoxyhexane) ester CAS NO: 763-69-9, diisopropyl peroxide dicarbonate CAS NO: 105-64-6, dibutyl peroxide dicarbonate CAS NO: 16215-49-9, di (3,5,5-trimethylhexanoyl) peroxide CAS NO: 3851-87-4, bis(2-ethylhexyl) peroxydicarbonate CAS NO: 16111-62-9, methyl ethyl ketone peroxide CAS NO: 1338-23-4, acetylacetone peroxide CAS NO: 37187-22-7, methyl isobutyl ketone peroxide CAS NO: 37206-20-5, tert-butyl hydroperoxide CAS NO: 75-91-2, di-tert-butyl peroxide CAS NO: 110-05-4, tert-amyl hydroperoxide CAS NO: 3425-61-4, di-tert-amyl peroxide CAS NO: 10508-09-5, peracetic acid CAS NO: 79-21-0, and 1,1,3,3-tetramethylbutyl hydroperoxide CAS NO: 5809-08-5.

4. The online continuous flow production method according to claim 1, wherein when an alkyl peroxide or a dialkylperoxide is produced, the oxidization substrate is an alcohol; a peroxycarboxylic acid is produced when the oxidation substrate is carboxylic acid; diacyl peroxide is produced when the oxidized substrate is acid chloride; peroxydicarbonate is produced when the oxidized substrate is chloroformate; biketal peroxide is produced when the oxidized substrate is ketone.

5. The online continuous flow production method according to claim 1, wherein the production time of the production process is equal to or less than 6 min.

6. The online continuous flow production method according to claim 1, wherein the target product organic peroxide is selected from the group consisting of diacyl peroxide and peroxydicarbonate; the content of chloride ion in the organic peroxide is ≤0.05 wt. %, and the content of $H_2O_2$ is ≤0.1 wt. %.

7. The online continuous flow production method according to claim 1, wherein the organic peroxide of the target product is the alkyl peroxide, and the content of $H_2O_2$ and di tert-butyl hydroperoxides in the alkyl peroxide is ≤0.1 wt. %.

8. The online continuous flow production method according to claim 1, wherein the organic peroxide of the target product is selected from the group consisting of dialkylperoxide, peroxycarboxylic acid and peroxyketal, and the content of $H_2O_2$ in the organic peroxide of the target product is ≤0.1 wt. %.

9. The online continuous flow production method according to claim 1, wherein the temperature of the oxidation process is 0 to 110° C.

10. The online continuous flow production method according to claim 1, wherein the temperature of the workup process is 0 to 50° C.

11. The online continuous flow production method according to claim 1, wherein the alkali is selected from the group consisting of water-soluble metal hydroxide, water-soluble quaternary ammonium hydroxide, water-soluble tertiary amine, water-soluble metal carbonate or water-soluble metal phosphate.

12. The online continuous flow production method according to claim 1, wherein the mass concentration of the acid solution is 50 to 90 wt. %.

13. The online continuous flow production method according to claim 1, wherein the concentration of the hydrogen peroxide is 30 to 50 wt. %.

14. The online continuous flow production method according to claim 1, wherein the molar ratio of acid to oxidation substrate is 0.5:1 to 1.1:1.

15. The online continuous flow production method according to claim 1, wherein the molar ratio of hydrogen peroxide to oxidation substrate is 0.5:1 to 2.5:1.

16. The online continuous flow production method according to claim 1, wherein the molar ratio of alkali to oxidization substrate is 1:1 to 1.4:1.

17. The online continuous flow production method according to claim 1, the oxidation unit at least comprises a first temperature zone, a second temperature zone and a third temperature zone being connected in series; the workup unit at least comprises a fourth temperature zone.

18. The online continuous flow production method according to claim 17, wherein the temperature in the first temperature zone is 0 to 60° C.;

the temperature in the second temperature zone is 30 to 110° C.;

the temperature in the third temperature zone is 0 to 50° C.;

the temperature in the fourth temperature zone is 0 to 50° C.

* * * * *